United States Patent [19]
Hamamoto et al.

[11] Patent Number: 5,732,469
[45] Date of Patent: Mar. 31, 1998

[54] PROSTHESIS AND A METHOD OF MAKING THE SAME

[75] Inventors: Shoichi Hamamoto; Hirokazu Amino; Noriyuki Ishida, all of Kyoto; Yasunori Tamura, Gamo; Yoichi Nishio, Kyoto; Masaru Ichimiya, Gamo, all of Japan

[73] Assignee: Kyocera Corporation, Kyoto, Japan

[21] Appl. No.: 437,781

[22] Filed: May 9, 1995

Related U.S. Application Data

[60] Division of Ser. No. 159,654, Dec. 1, 1993, Pat. No. 5,496,372, which is a continuation-in-part of Ser. No. 48,408, Apr. 15, 1993, abandoned.

[30] Foreign Application Priority Data

| Apr. 17, 1992 | [JP] | Japan | 4-98282 |
| Apr. 19, 1993 | [JP] | Japan | 5-91654 |

[51] Int. Cl.$^6$ ............................................. B23P 15/16
[52] U.S. Cl. ................................................... 29/896.6
[58] Field of Search ........................... 29/896.6, 896.8; 623/16

[56] References Cited

U.S. PATENT DOCUMENTS

| 3,855,638 | 12/1974 | Pilliar | 623/16 |
| 4,608,052 | 8/1986 | Van Kampen et al. | 623/18 |
| 4,644,627 | 2/1987 | Palazzo | 29/423 |
| 4,660,755 | 4/1987 | Farling | 623/18 |

Primary Examiner—P. W. Echols
Attorney, Agent, or Firm—Loeb & Loeb LLP

[57] ABSTRACT

A prosthesis for the replacement of hard tissues of human bones and joints, comprising a porous lamination component of metal thin sheets, each having a plurality of through holes and a thickness of 150 μm or less, and being unharmful to the living body, the porous lamination component being formed such that the sheets are laid over one another and are then diffusion-bonded therebetween into one body by heating so that the through holes communicate with one another in the direction of the thickness thereof, and the prosthesis being entirely or partially composed of the porous lamination component. The present invention also relates to a method of making such a prosthesis. The present invention can provide prostheses which are not required to be replaced again, thereby imposing a less burden to patients.

5 Claims, 42 Drawing Sheets

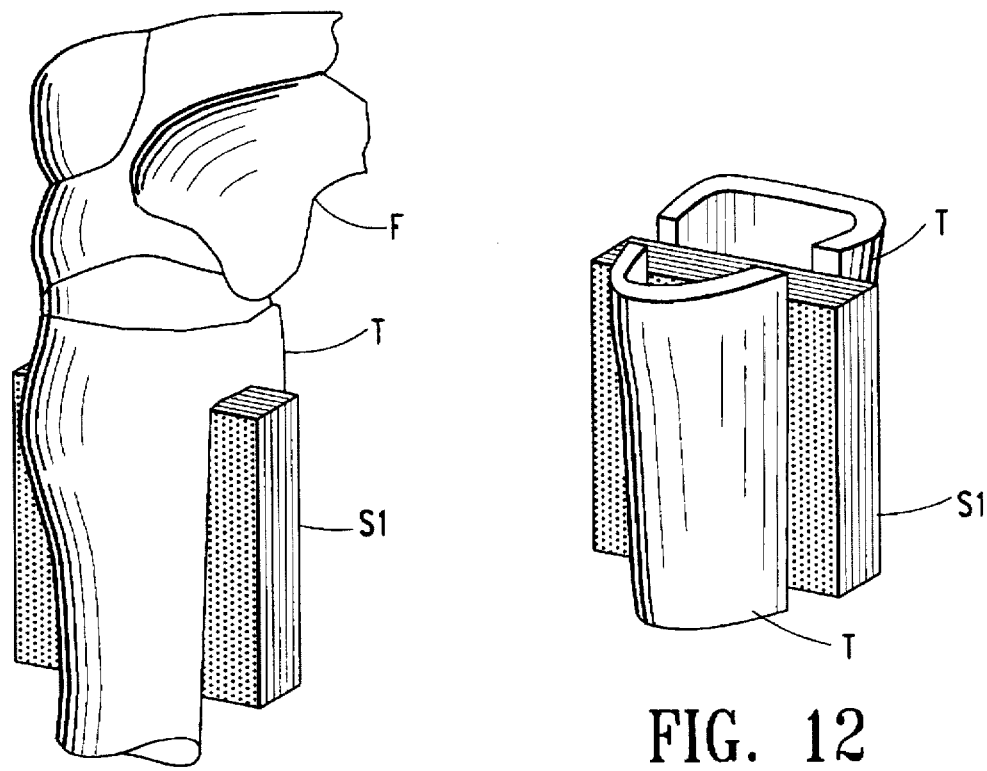
FIG. 11
FIG. 12
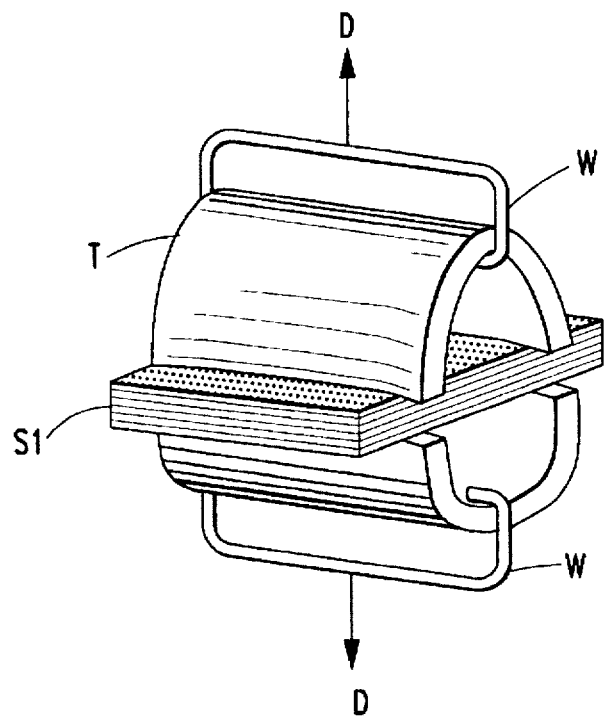
FIG. 13

PROSTHESIS AND A METHOD OF MAKING THE SAME

This is a division of application Ser. No. 08/159,654 filed on Dec. 1, 1993, now U.S. Pat. No. 5,496,372 which is a continuation-in-part application of Ser. No. 08/048,408 filed Apr. 15, 1993, now abandoned.

BACKGROUND OF THE INVENTION

1. Field of the Invention

The present invention relates to a prosthesis for the replacement of hard tissues such as human bones or joints having significantly deteriorated or lost functions thereof, and more particularly to a prosthesis having a porous surface structure capable of allowing bone tissues to penetrate so that the support/fixture characteristics of the joining section between the prosthesis and the living tissues can be enhanced. The present invention also relates to a method of making such a prosthesis.

2. Prior Art

As conventional prostheses having porous surface structures capable of allowing bone tissues to penetrate, a plurality of prostheses have been proposed as follows:

(1) A metallic prosthesis having sintered and adhered metallic beads on the surface thereof, as disclosed by U.S. Pat. No. 3,855,638 and U.S. Pat. No. 4,644,942.

(2) A metallic prosthesis having compressed metallic meshes diffusion-bonded onto the surface thereof by heating at high temperature, as disclosed by European Patent No. 0178650 and U.S. Pat. No. 4,660,755.

(3) A prosthesis having porous metallic sheets secured mechanically to the surface thereof, as disclosed by GB No. 2142830A.

(4) A prosthesis having a porous surface structure with small through holes made by laser processing, as disclosed by U.S. Pat. No. 4,608,052.

(5) A prosthesis having a cast porous component secured to the surface thereof, as disclosed by Japanese Laid-open Patent Application No. 3-123546.

(6) A metallic prosthesis having a surface structure with through holes, the shape of which is almost similar to that of the cancellous bone tissue, as disclosed by Japanese Laid-open Patent Application No 3-29649.

(7) A prosthesis having a porous lamination component comprising laminated thin sheets, each having through holes provided by punching or etching and a thickness of 150 to 500 μm, made by applying a compression load and heating, or a prosthesis whose surface is partially or entirely coated with the porous lamination component, as disclosed by Japanese Laid-open Patent Application No. 3-49766.

The above-mentioned prostheses, however, have the following problems. The prosthesis (1) has a low volume porosity (the ratio of the volume of pores to the entire volume of the porous component thereof); it is generally said that the typical volume porosity of the above-mentioned conventional prostheses is about 35%. When this volume porosity is low, the relative volume of the bone tissue is small even if the bone tissue completely fills up all pores. Accordingly, the strength of the bonding between the prosthesis and the bone joined thereto is not sufficiently large. In the case of the prosthesis wherein metallic beads are attached to the surface thereof, it is known that the mechanical strength of the prosthesis' base material is significantly lowered by high temperature in the sintering process wherein the beads are attached. According to a report, for example, the fatigue strength of such a prosthesis is lowered to about 1/5 of that of the base material. The sintering process thus significantly adversely affects the durability of the prosthesis when used in the living tissue. In addition, since the bonding strength obtained among the above-mentioned beads is low, the beads may drop after sintering and may be in danger of penetrating articulation surfaces.

In the above-mentioned prosthesis (2), the volume porosity of the porous lamination component thereof is about 50% and the fatigue strength of the porous lamination component is about 70% of the base material thereof, showing a considerable improvement when compared with the above-mentioned prosthesis (1). It is however difficult to control the size and shape of small through holes within desired ranges in the compression process. As a result, the size and shape of the small through holes to be formed are not best suited for the penetration and ingrowth of the bone tissue. Furthermore, the above-mentioned porous lamination component has a disadvantage of generating a great difference in the size and shape of the through holes between those formed in the flat surfaces and those formed in the curved surfaces of the prosthesis because of the difference in the compression load. This changes the degree of the penetration of the bone tissue into the small through holes depending on the portion of the prosthesis, and causes the problem of generating different strength of the bonding between the porous lamination component and the bone to be joined depending on the portion of the prosthesis.

In the case of the prosthesis (3), since the above-mentioned sheets are mechanically bonded to the main body, the sheets cause micro-movements, resulting in wear or melting of the metallic structure thereof, and also resulting in the removal of the sheets in the worst case. This prosthesis is thus not applicable to portions having complicated curved surfaces. In addition, the cost of making the prosthesis is not inexpensive.

The above-mentioned prosthesis (4) has a surface structure having through holes with a diameter of about 300 μm disposed regularly. The through holes however are not open pores communicating with one another but closed pores, thereby preventing bio-liquid from flowing among the bone cells, causing the problem of necrosis at the leading ends of the bone cells.

In the case of the above-mentioned prosthesis (5), since the porous lamination component thereof is made by casting, it is difficult to apply the porous lamination component to portions having complicated curved surfaces. Furthermore, the production cost is high because casting is used.

The above-mentioned prosthesis (6) has a surface structure similar to that of a cancellous bone in size and shape. The size and shape of the through holes in this structure are, however, not best suited for the penetration of bone tissues, thereby causing the problem of preventing bone tissues from sufficiently penetrating the through holes.

In the case of the above-mentioned prosthesis (7), since the thin sheets thereof are as thick as 150 to 500 μm, the porous lamination component thereof cannot be used for complicated curved surfaces or small-diameter cylindrical surfaces. Furthermore, the shape and arrangement of the holes are significantly deformed and dislocated by lamination and compression. It is therefore difficult to properly control the through hole shape best suited for the penetration of bone tissues, thereby causing the problem of preventing bone tissues from sufficiently penetrating the through holes.

SUMMARY OF THE INVENTION

To solve the above-mentioned problems, the object of the present invention is to provide a prosthesis for the replacement of hard tissues of human bones or joints, comprising a porous lamination component of metallic thin sheets, each having a plurality of through holes and a thickness of 150 μm or less and being unharmful to the living body, or a prosthesis which is partially composed of the above-mentioned porous lamination component at a desired surface portion of the prosthesis base. The term "base" here implies a portion to be embedded in the living bone tissue (hereinafter only referred to as "base"). Another object of the present invention is to provide a method of making such a prosthesis.

BRIEF DESCRIPTION OF THE DRAWINGS

FIG. 11 is a schema illustrating an animal experiment using the porous lamination component shown in FIG. 3.

FIG. 12 is a view similar to FIG. 11, illustrating another animal experiment.

FIG. 13 is a view similar to FIG. 11, illustrating still another animal experiment.

DETAILED DESCRIPTION OF THE INVENTION

According to the present invention, porous thin sheets 1, 2, . . . , each having a thickness of 150 μm or less, are laminated and formed in a desired prosthesis shape, or laminated on the flat or curved surface of a prosthesis base. In the thin sheets 1, 2, . . . , small through holes H having a shape suited for the penetration and ingrowth of a plurality of bone cells are provided. In addition, a prosthesis surface having a porous lamination component S1 with a three-dimensional cubic structure is formed by slightly displacing the positions of the through holes disposed in laminated thin sheets in the direction of the depth. The bone tissues penetrated and grown in the three-dimensional space inside the porous surface functions to firmly support the prosthesis in the living body by utilizing its cubic structure, thereby preventing the micro-movement of the prosthesis. Furthermore, by coating a bio-compatible material, in which bone cells can easily grow, on the laminated thin sheets, the penetration of bone cells can be promoted more promptly after the replacement operation of the prosthesis, thereby permitting earlier fixture to the bone to be joined. Moreover, when a prosthesis made by laminating the thin sheets 1, 2, . . . having through holes H with an effective diameter of 100 to 400 μm is secured with bone cement, the fixture performance between the bone cement and the prosthesis can be enhanced significantly.

EXAMPLES

Referring to the accompanying drawings, the examples of the present invention will be explained specifically.

Example 1

Figure 1:
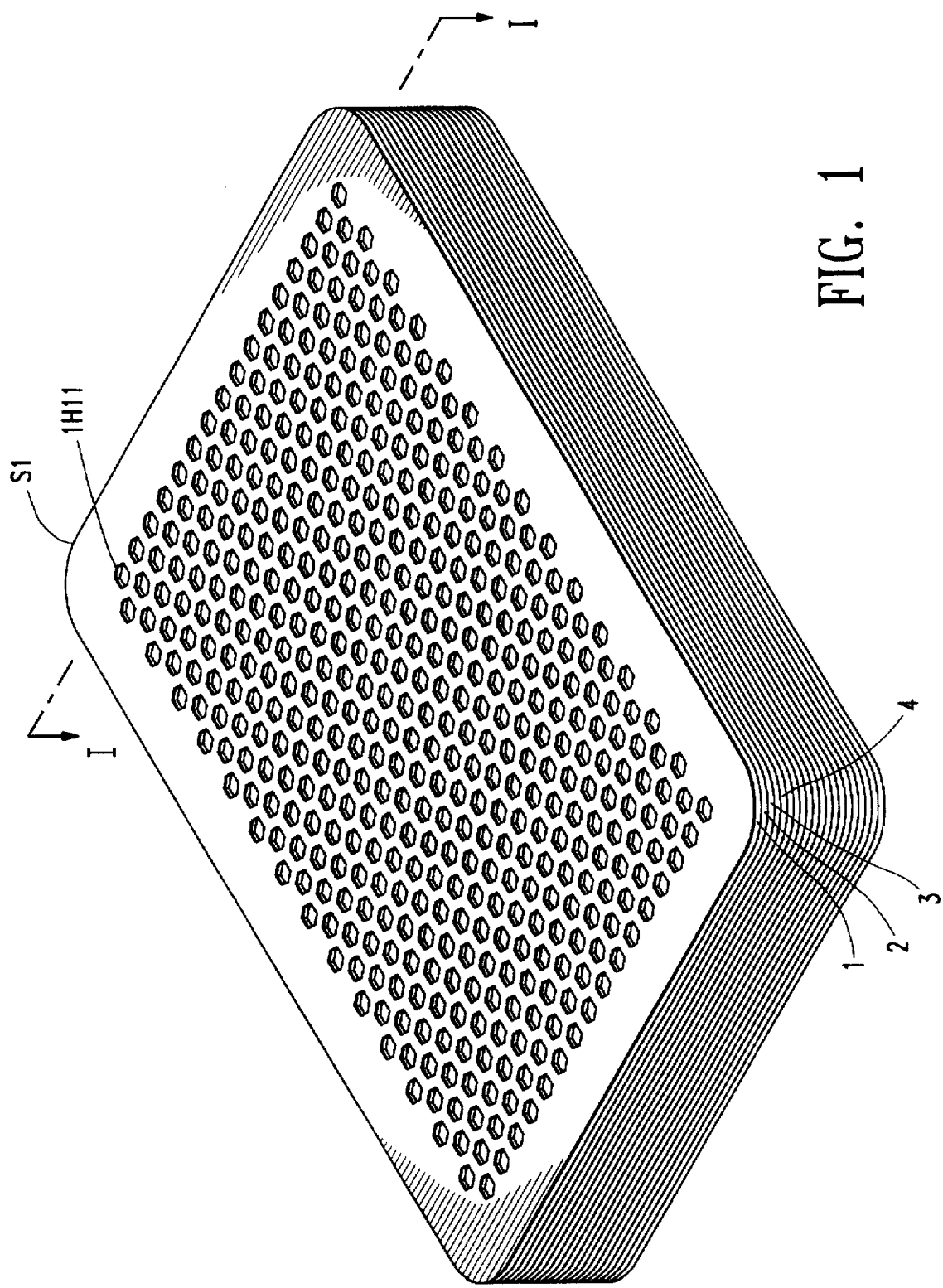
FIG. 1 is a perspective view of a porous lamination component of an example of the present invention

FIG. 1 is a perspective view of a porous lamination component S1 comprising the whole of a prosthesis, or a part or the whole of the base surface of a prosthesis of the present invention. The porous lamination component S1 measures 10×15×2 mm. It has a sequentially laminated structure including 20 layers of porous thin sheets 1, 2, . . . , each having a thickness of 100 μm and a plurality of through holes. The thin sheets 1, 2, . . . are made of pure titanium. After the thin sheets 1, 2, . . . were positioned properly while being laminated, and secured temporarily by placing a very light weight on them or by using adhesive, they were heated at about 900° C. in a vacuum sintering furnace so that they were bonded mutually. The heater of the sintering furnace is made of molybdenum. The heating process can be conducted in an atmosphere of inert gas such as argon. The bonding of the thin sheets 1, 2, . . . was conducted by diffusion-bonding between metal atoms. The thin sheets 1, 2, . . . were positioned by utilizing the rectangular sides thereof as reference sides. In the process inside the vacuum furnace, although the overlap of the through holes H may be dislocated slightly, the amount of the dislocation is about 20 μm and is almost negligible for proper production. If more precise overlap is necessary, or if the external shape of the porous lamination component S1 has a shape other than a cube and has not any flat surface portions which can be used as reference surfaces, positioning holes (not shown) should preferably be provided at the four corners of the thin sheets 1, 2, . . . After the thin sheets 1, 2, . . . were diffusion-bonded mutually in this way, no special change was recognized in the appearance and dimensions of the porous lamination component S1 and no deteriorated layer was recognized.

Figure 2:
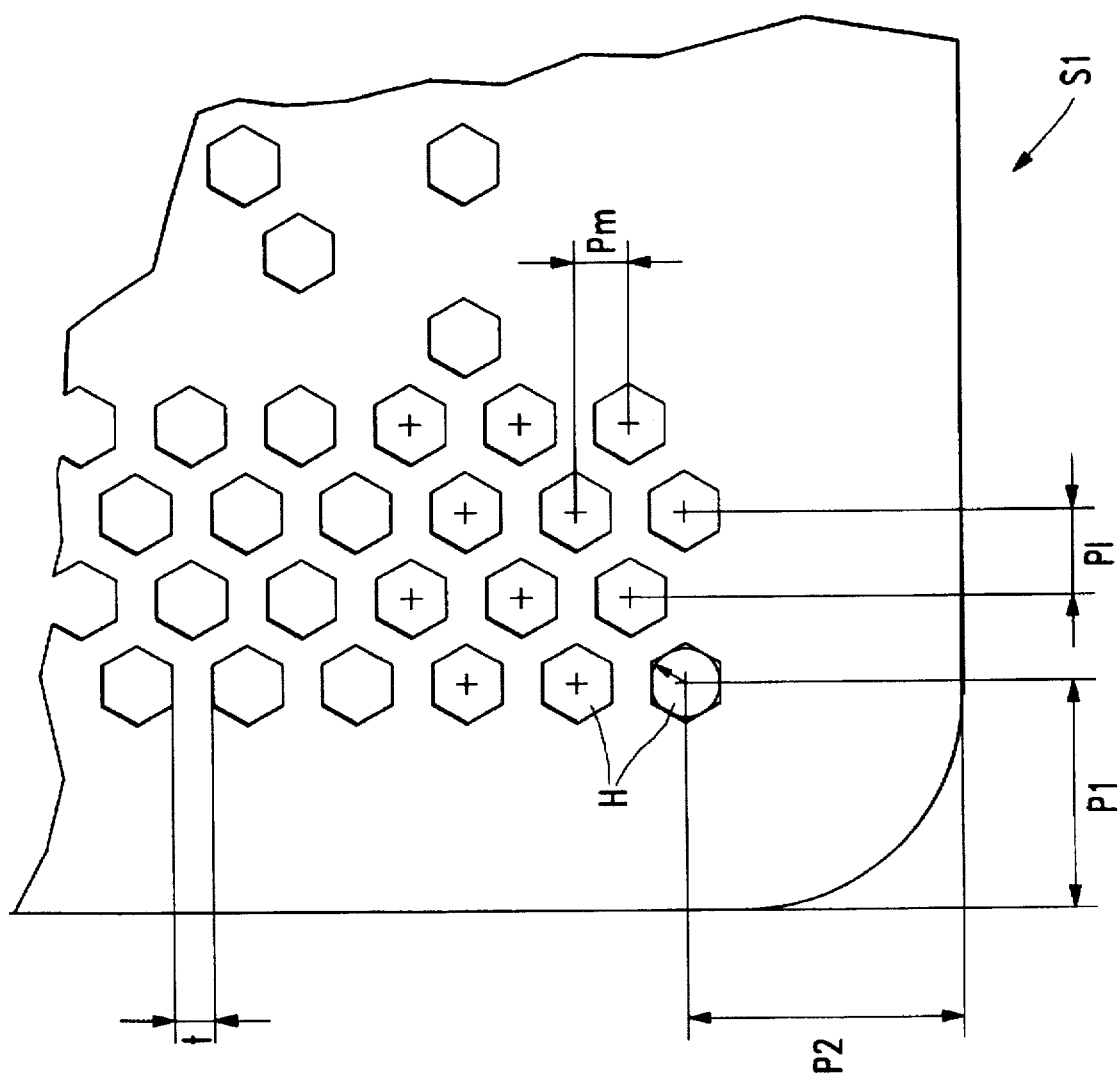
FIG. 2 is a plan view illustrating the arrangement of through holes in the thin sheets of the porous lamination component shown in FIG. 1.

FIG. 2 shows a magnified view of regular hexagonal through holes H formed in the thin sheets 1, 2, 3, 4, . . . of the above-mentioned porous lamination component S1. The shape of the regular hexagonal through holes H is one of shapes suited for easy penetration and dense ingrowth of osteon, the minimum unit of bone tissues. The shape is also suited for allowing the highest density filling arrangement of the through holes in the same way as that shown in honeycombs and crystal structures. As the dimension of a pore which permits bone tissues to penetrate easily, the diameter of the inscribed circle of the through hole H of this example was determined to be about 350 μm. Since the etching method as described below was used to form the through holes H in this example, the central sectional portion of the through hole H was raised. The diameter of the inscribed circle at the mostly raised portion became about 300 μm. The porous lamination component S1 was designed as shown in FIG. 2; the horizontal width of the non-pore fringe portion P1=1.05 mm, the vertical width of the non-pore fringe portion P2=1.27 mm, the horizontal interval between the through holes Pl=500 μm, and the vertical interval between the through holes Pm=433 μm, thereby most densely arranging the through holes H with an effective diameter of 350 μm. The space t between the through holes H resulted in 150 μm. The volume porosity of the pores in the porous lamination component S1 designed in this way is about 50% per unit volume, that is, the volume porosity of the porous lamination component S1 is 50%. In this way, the volume porosity of the porous lamination component S1 can be easily controlled by appropriately adjusting the effective diameter of the through holes H, the interval between the through holes H and the combination of lamination layers. For example, if P1=450 μm and Pm=383 μm in the above example, the volume porosity can be changed to about 60%. Furthermore, if P1=450 μm, Pm=383 μm and the effective diameter of the through holes H is 400 μm in the above example, the volume porosity can be changed to about 75%. The volume porosity should preferably be as large as possible to make the amount of bone tissues to penetrate as much as possible.

The above-mentioned through holes H were formed by an etching method. The through holes H can also be formed by laser processing or punching.

Figure 3:
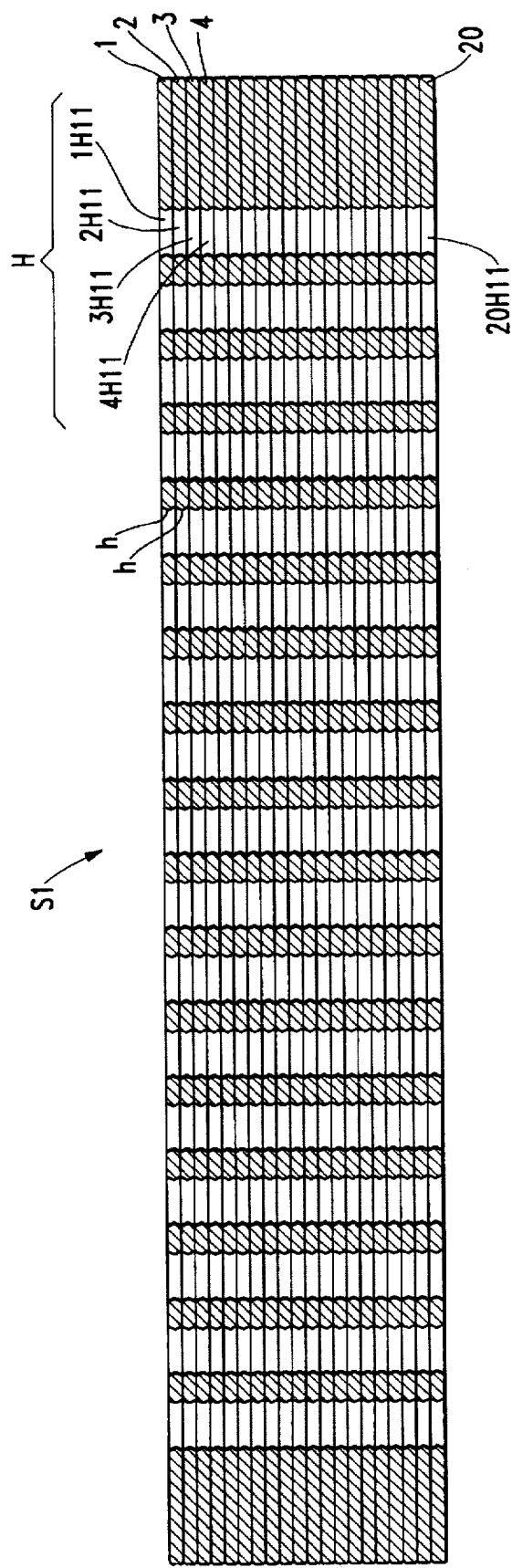
FIG. 3 is a view taken on line I—I of FIG. 1.

FIG. 3 is a sectional view of the porous lamination component S1 taken on line I—I of FIG. 1. To design the distribution of the through holes H, the through hole H disposed at the n-th line and the m-th column of the first layer is defined to be represented as 1Hnm. The through hole H represented by 1H11 is a through hole disposed at the first line and the first column of the first layer. The thin sheets 1, 2, . . . with a thickness of 100 µm are laminated and the through holes 1H11 and 2H11 communicate with each other. In actual practice, however, the layers of the porous lamination component S1 are often dislocated slightly as described above. When the thin sheet is corroded on both sides thereof in the etching liquid showering process to form through holes H, the cross section of the sheet has a shape similar to a rhombus because of the projection section h projecting toward the center of the through hole H as shown in the figure, and the angle of the inclined surface thereof is in the range of about 30 to 45 degrees. If the thin sheet is etched on the one side thereof, the cross section of the sheet has a shape similar to an isosceles triangle. Whether the thin sheet is etched on both sides or on one side is determined by considering the shape of the prosthesis to be used and the biomechanical conditions at the hard tissue portion to be replaced. More particularly, it is necessary to consider what kind of stress and how much stress remains on the surface of the porous lamination component S1. In addition, when bone cement is used for fixture, the porous lamination component S1 should be designed so that bone cement can easily penetrate the through holes H and cannot come out easily after polymerization.

Figure 4:
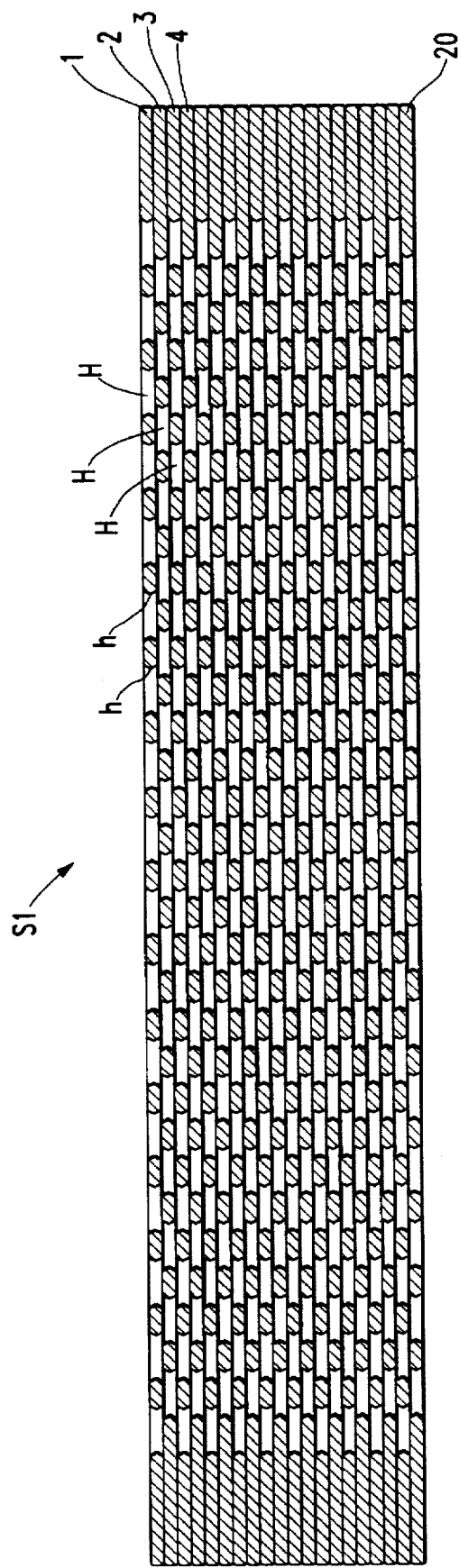
FIG. 4 is a vertical sectional view of the porous lamination component of another example of the present invention.

The porous lamination component S1 processed as described above has slight dislocations at laminated portions. For example, the positions of the through holes 1H11 and 2H11 are dislocated slightly from their designed positions. If the through holes H in the thin sheets 1, 2, . . . are designed to be disposed alternately as shown in FIG. 4, more spaces can be provided to guide bone tissues. With this structure, bone tissues can penetrate the prosthesis for an extended period of time, thereby being more effective for the support of the prosthesis. This kind of uniform plan view shape and three-dimensional structure of the through holes H can be formed on any prosthesis surfaces by utilizing the present invention. The plan view shape of the through holes H should preferably be a regular hexagonal shape having the highest density filling efficiency, and should also be a shape capable of increasing the volume porosity as large as possible. In addition, the through holes H adjacent to one another should preferably have open three-dimensional structures contacting one another. Furthermore, to shorten the period requiring for permitting bone tissues to penetrate, the through holes H should preferably be coated with a bio-active living body material having affinity to bone tissues. As the material used for coating, bioglass ceramics, chitin, chitosan and gelatin can be nominated. In particular, when no bio-active living body material is coated, titanium oxide coating or titanium nitride coating superior in corrosion resistance in the living body should preferably be used to prevent metal ions from flowing out. Moreover, when bone cement is used to secure the prosthesis, the through holes H should preferably be coated with an agent, such as a silane coupling agent, which can strengthen the force of adhesion to bone cement.

Figure 7:
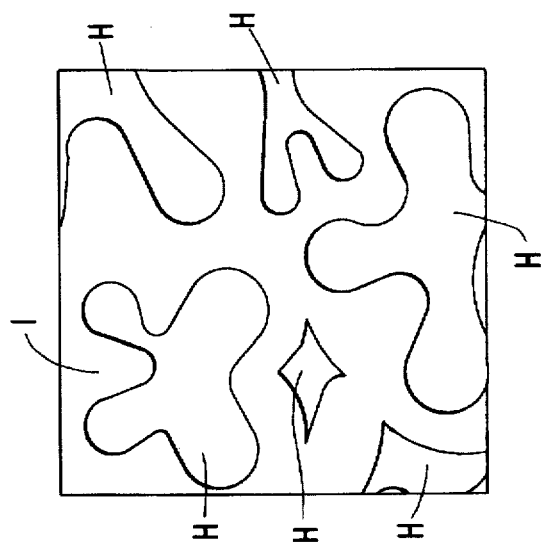
FIG. 7 is a plan view illustrating still another flat surface shape of a thin sheet of the present invention.
Figure 6:
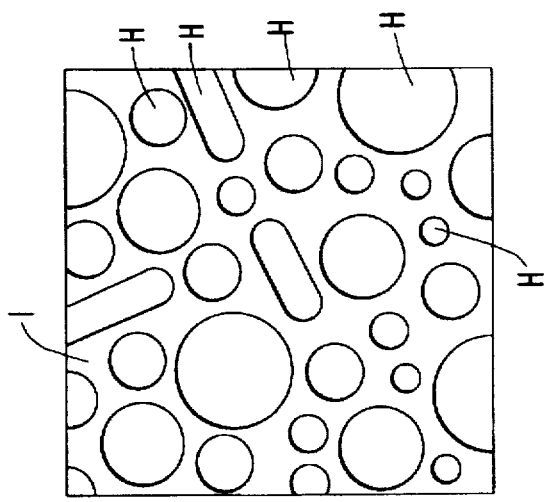
FIG. 6 is a plan view illustrating another flat surface shape of a thin sheet of the present invention.
Figure 5:
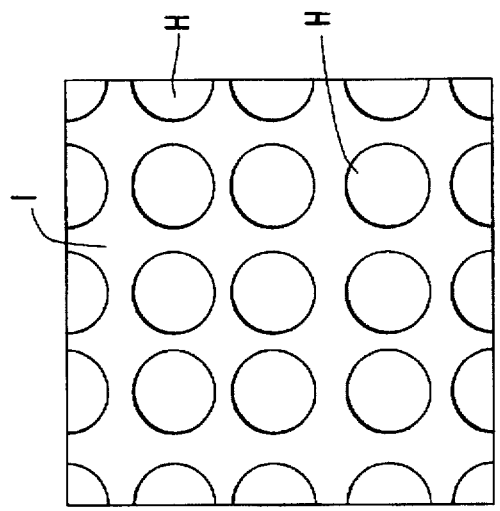
FIG. 5 is a plan view illustrating a flat surface shape of a thin sheet of the present invention.

FIGS. 5, 6 and 7 show various plan view shapes of the through holes H. The plan view shapes of the through holes H should be suited for the penetration of bone cells. FIG. 5 shows the through holes H disposed at the highest density arrangement. FIG. 6 shows the through holes H with various diameters. Although it is generally said that pores with an inscribed circle diameter of 75 to 350 µm are suited for promoting the penetration of bone cells, a plan view shape having distributed pores with various diameters in a constant area, such as that shown in FIG. 6, can also be considered to be effective. This kind of plan view shape can also be obtained easily by utilizing the present invention. In some cases, indeterminate forms of through holes H shown in FIG. 7 may be desirable. Depending on the kind of bone cells, a proper response may not necessarily be obtained by circular through holes, but a tapered shape may be preferable.

Figure 8:
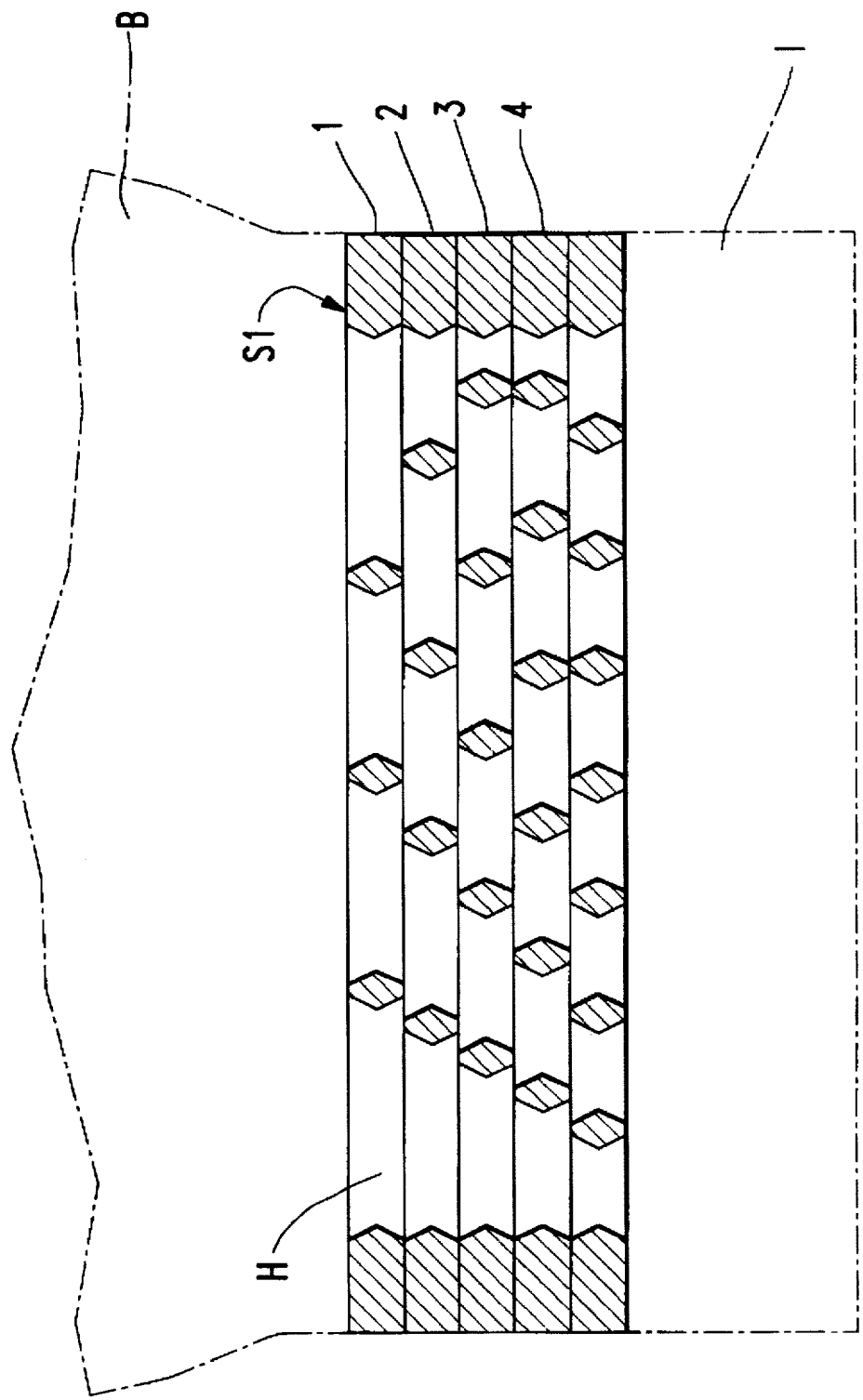
FIG. 8 is a vertical sectional view of a porous lamination component of the present invention, illustrating a lamination condition of the through holes.
Figure 9:
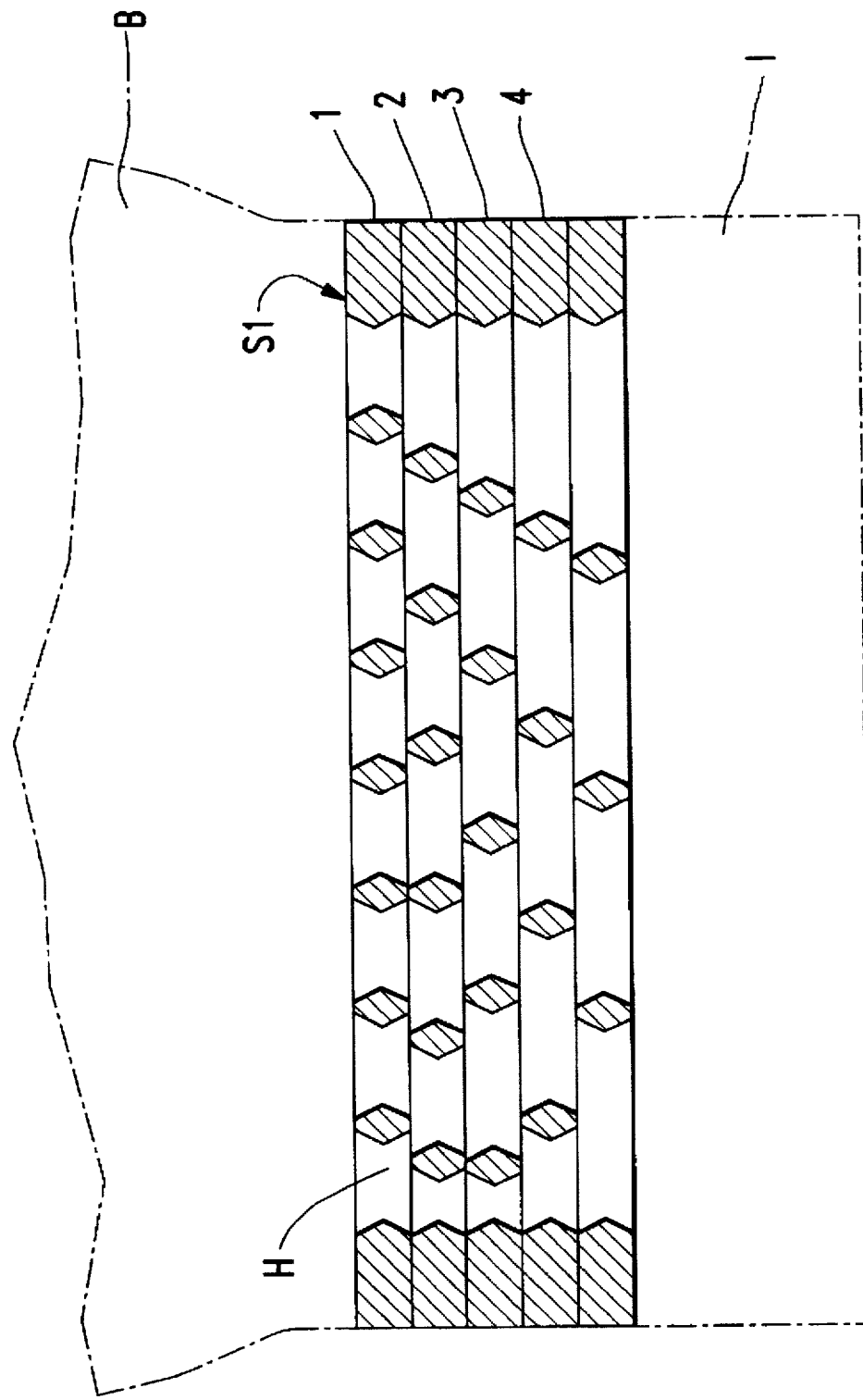
FIG. 9 is a view similar to FIG. 8, illustrating another lamination condition of the through holes.
Figure 10:
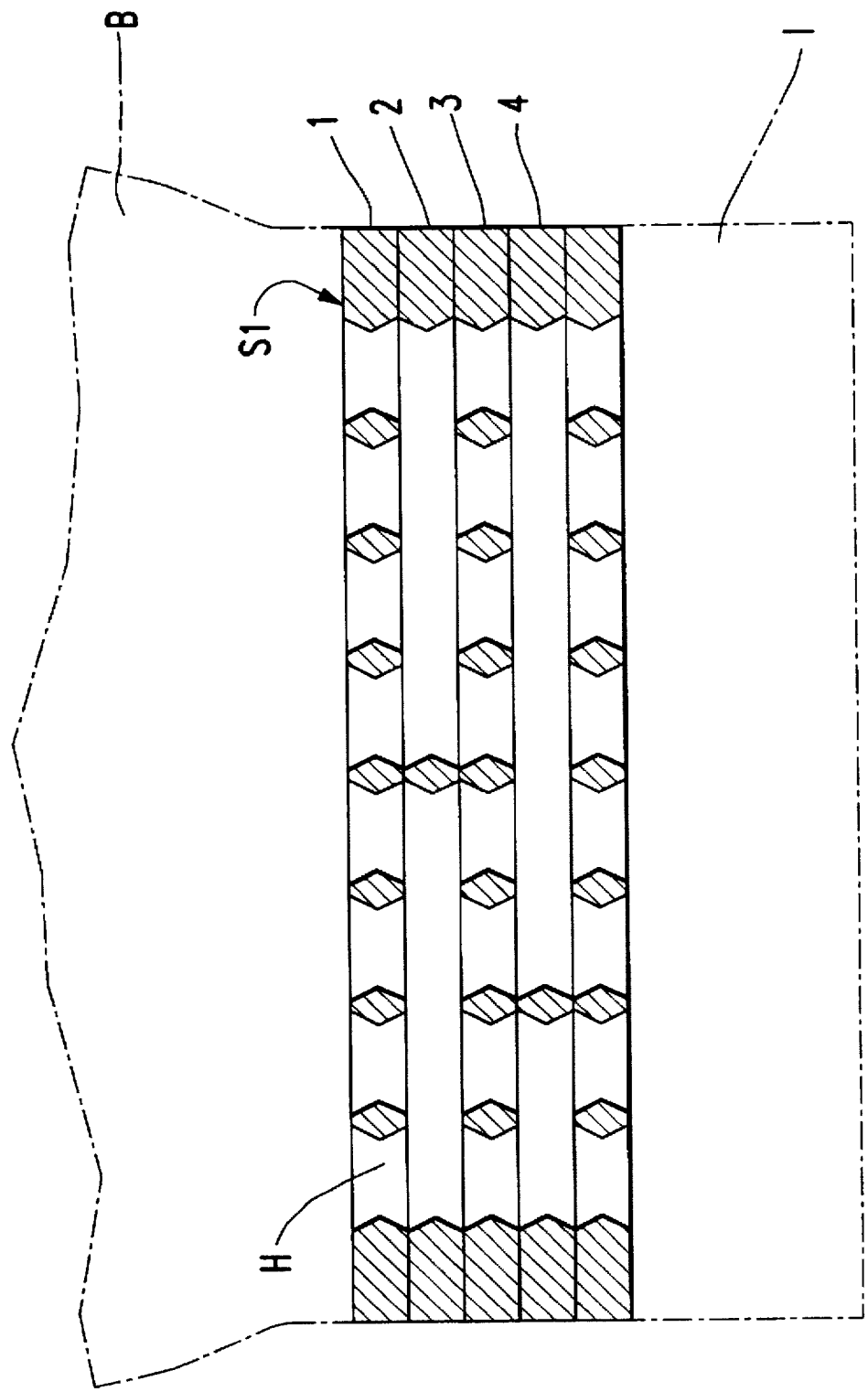
FIG. 10 is a view similar to FIG. 8, illustrating still another lamination condition of the through holes.

FIGS. 8, 9 and 10 show the sectional structures of the through holes H in the laminated thin sheets 1, 2, . . . FIG. 8 shows a sectional structure wherein the effective dimensions of the through holes H disposed in the thin sheets 1, 2, . . . become smaller as the through holes H are disposed closer to the prosthesis base I from the bone tissue side B. FIG. 9 shows a sectional structure which is opposite to that shown in FIG. 8. This sectional structure is particularly effective when a tension load is applied to the porous lamination component surface. FIG. 10 shows a sectional structure wherein the areas of the through holes H in the second and fourth layers are especially larger than those of the through holes in the other layers. When the shape of the prosthesis base I is curved and the curvature of the shape is small, the positional relationship among the thin sheets are dislocated slightly. Although it is possible to design the thin sheets 1, 2, . . . by considering the effect of the slight dislocation previously estimated, the dislocation can be neglected to some extent by using the structure shown in FIG. 10. In addition, it is also said that the structure wherein the diameters of the through holes H are made larger in the upward or downward direction is suited for the ingrowth of bone tissues.

FIG. 11 shows a schema illustrating the porous lamination component S1 made as described above and used for an animal experiment to examine the effectiveness thereof. The porous lamination component S1 used for this experiment has through holes H which pass through straight in the vertical direction as shown in FIG. 3. The effective diameter of the through hole H is 350 µm and the volume porosity of the porous lamination component S1 is 60%. The experiment was conducted in accordance with the method described in the Journal of Biomedical Materials Research (hereinafter referred to as "JBMR"), Vol. 20, 1295–1307 (1986). The porous lamination component S1 was embedded at a position about 3 cm from a mesial tibia T of rabbits. The porous lamination component S1 was cleansed, autoclaved, and wetted with a saline solution including a dissolved antibiotic. The porous lamination component S1 was then embedded into a gutter by pounding it with a hammer. The periosteum, muscle, fascia and skin were stitched up together in accordance with the conventional methods. After the antibiotic was given, the treatment portion was laid quietly. Each rabbit was allowed to move freely in a cage (50×80×40 cm) and was fed with solid food and water.

The rabbits were killed four and six weeks after operation. As shown in FIG. 12, the porous lamination component S1 and a part of the tibia T around the porous lamination component were taken out. After about two hours, without formalin fixation, a wire W was passed through the tibia T as shown in FIG. 13 and the adhesion strength D of the structure was measured by using an instron testing machine. The loading condition of the instron testing machine was given at a cross head speed of 3.5 cm/min in accordance with the above-mentioned method.

Figure 14:
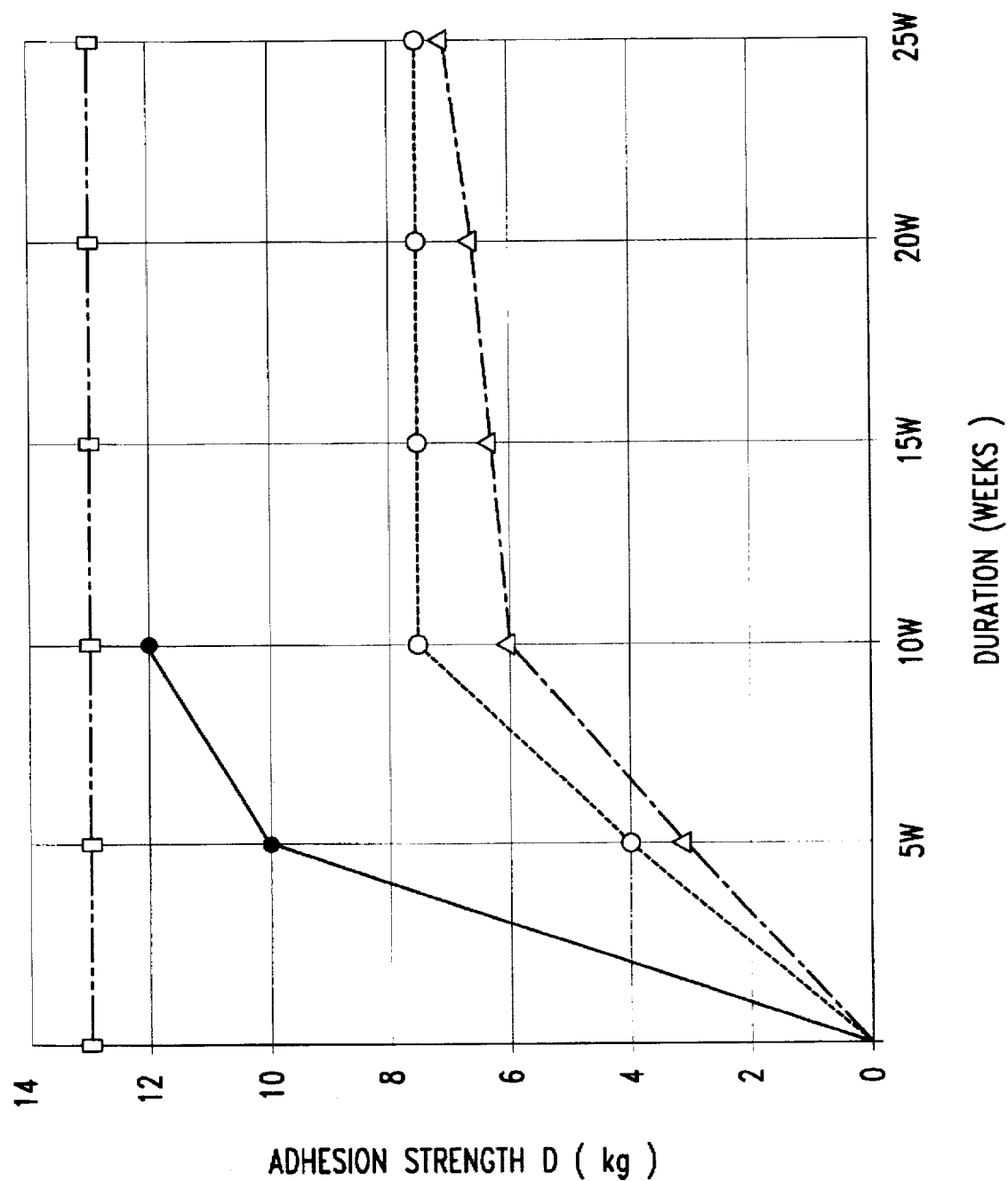
FIG. 14 is a graph illustrating the measurement results of the adhesion strength of a porous lamination component of the present invention.

FIG. 14 is a graph illustrating the measurement results of the adhesion strength D. The points marked • indicate the adhesion strength of the porous lamination component S1 of the present invention. The adhesion strength of the porous lamination component S1 was about 10 kg five weeks after adhesion. After ten weeks, the adhesion strength of the S1 was about 12 kg. The adhesion strength per unit area was 6 kg/cm$^2$ after five weeks and 8 kg/cm$^2$ after ten weeks. Breakage occurred in the tibia T attached to the porous lamination component S1. No separation was observed at the interfaces of the thin sheets of the porous lamination component S1. The points marked o indicate the adhesion strength of the bioglass ceramics reported in the above-mentioned literature. It was reported that the average adhesion strength was 7.61 kg after ten weeks and 7.24 kg after 25 weeks. As reported in JBMR, Vol. 23, 781–808 (1989), the average adhesion strength of hydroxyapatite was 6.40 kg after eight weeks and 6.86 kg after 25 weeks as indicated by the points marked Δ. The points marked □ indicate the strength of the bone. It was reported that the average adhesion strength was 11.96 kg after 25 weeks according to JBMR, Vol. 19, 685–698 (1985). Since these experiments were conducted in the same conditions, the values of the measurement results can be used for comparison. According to these results, it is found that the porous lamination component S1 of the present invention is superior to the bioglass ceramics and hydroxyapatite, which are assumed to be the most bio-active materials among the currently available living body materials in terms of the performance of bonding and adhesion to bone tissues. It is also found that the adhesion strength of the prosthesis reaches a value almost similar to the strength of the bone in a short period of about ten weeks.

Figure 15:
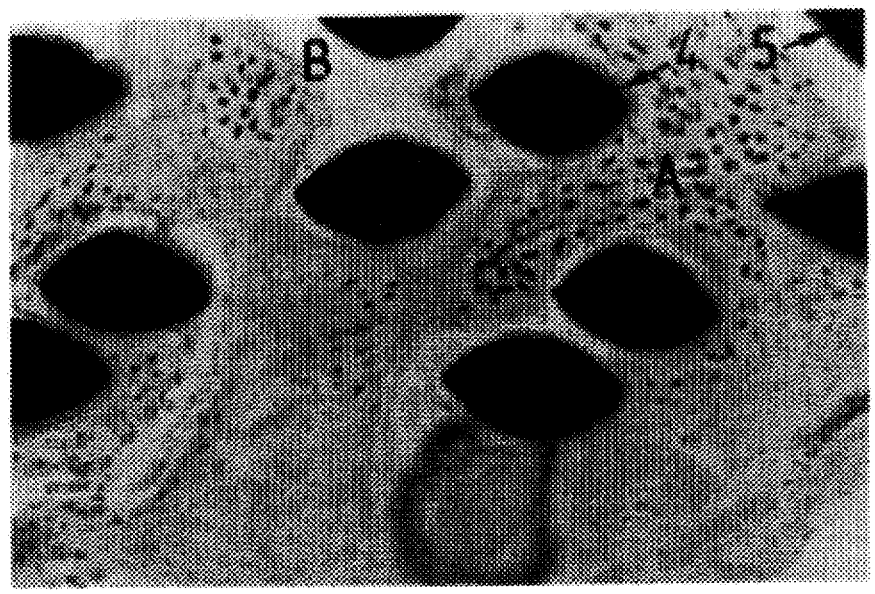
FIG. 15 is a microphotograph illustrating a histopathological examination result of a porous lamination component of the present invention used for an animal experiment.
Figure 16:
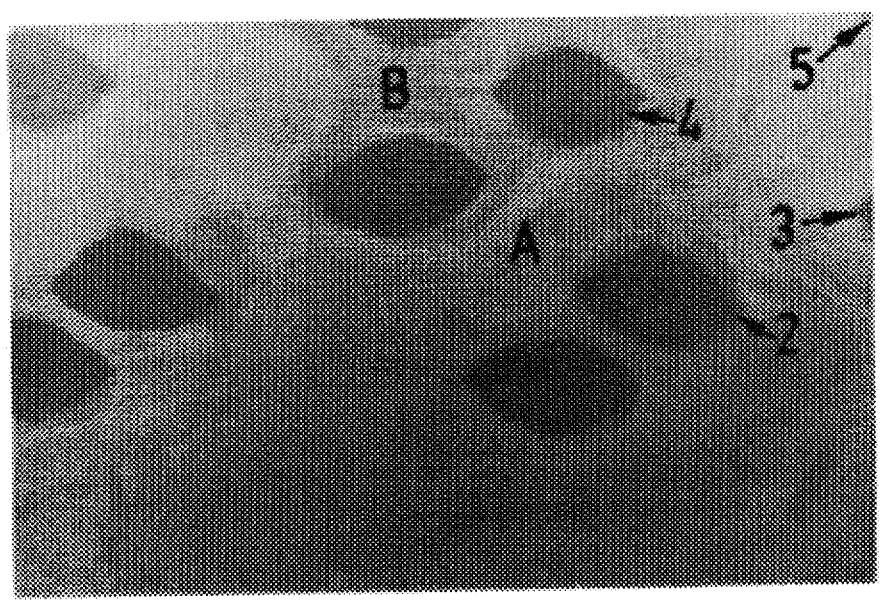
FIG. 16 is a microphotograph illustrating another histopathological examination result of a porous lamination component of the present invention used for an animal experiment.
Figure 17:
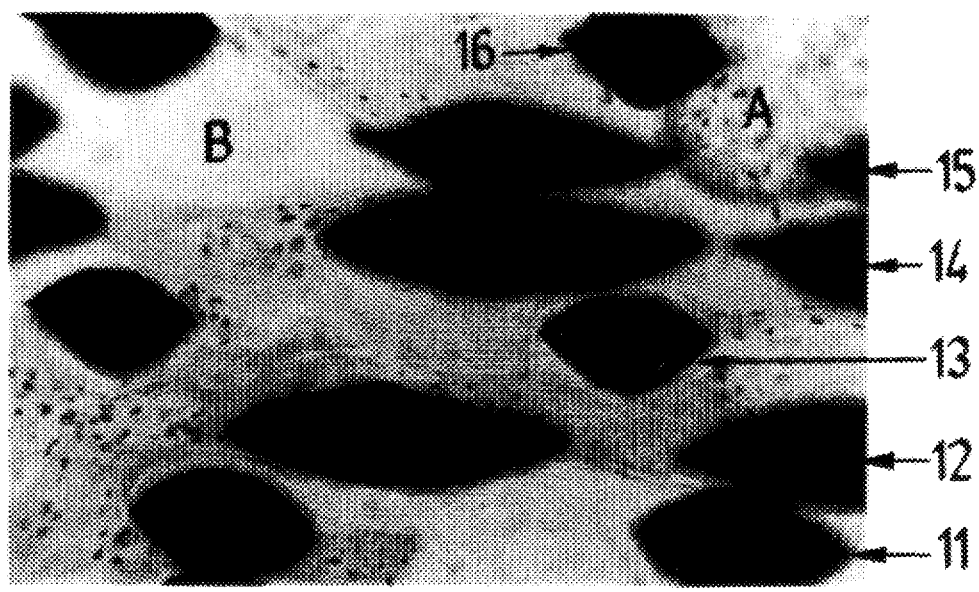
FIG. 17 is a microphotograph illustrating still another histopathological examination result of a porous lamination component of the present invention used for an animal experiment.

FIGS. 15, 16 and 17 are microphotographs illustrating the histopathological examination results of the porous lamination component S1 used for the adhesion strength measurement tests.

The bone tissues obtained after the adhesion strength tests and the porous lamination component S1 were subjected to dehydration and resin embedding in accordance with the conventional methods, and sliced in the direction perpendicular to the longitudinal axis of the tibia T, then manually processed to obtain ground sections Z with a thickness of up to about 50 μm. The sections were observed by using a light microscope in accordance with the normal light microscopy method and the fluorescent microscopy method.

FIG. 15 is a microphotograph at 5500 magnifications. It is found that bone tissue A and marrow tissue B coexist in the through holes H in the regions of the thin sheets 1 to 5. In addition, blood vessel tissues and new osteoblasts were observed with the naked eye, although they were not taken clearly on the microphotograph. FIG. 16 shows a fluorescent microscopic image of the image shown in FIG. 15.

FIG. 17 shows the regions corresponding to the thin sheets 11 to 15. Although the amount of the bone tissue A is smaller, there are no great differences in the calcification degree and the adhesion strength of the bone tissue.

As shown in FIGS. 15 to 17, the bone tissue A penetrated almost all through holes H of the thin sheets 1 to 20 of the porous lamination component S1 grew in the through holes. It is found that the tissue A is a normal bone tissue including marrow tissue B. This result indicates that a complex substance is formed between the surface of the porous lamination component of the present invention and the bone and that the metallic thin sheets reinforce the bone tissues. In addition, it is found that the bonding strength of the porous lamination component S1 is sufficient and that the force of adhesion to the bone is almost equal to the breakage force of the bone itself.

Next, other samples of the porous lamination component S1 comprising thin sheets 1, 2, . . . having different thickness values listed in Table 1 (different from the thickness of the thin sheets of the porous lamination component S1 used for the above-mentioned experiments) were made in accordance with the above-mentioned method. These samples of the porous lamination component S1 were used for the same animal experiments as those described above and the adhesion strength values were measured after ten weeks. The measurement results are shown in Table 1.

TABLE 1

| Sample No. | Thickness of thin sheet (μm) | Adhesion strength (kg/cm$^2$) |
|---|---|---|
| 1 | 5 | 9.1 |
| 2 | 10 | 12 |
| 3 | 50 | 12 |
| 4 | 100 | 12 |
| 5 | 150 | 12 |
| 6 | 175 | 8.3 |

As obviously indicated by Table 1, when the above-mentioned thickness is in the range of 10 to 150 μm, the adhesion strength is 12 kg/cm$^2$. This value is almost equal to the strength of the bone as described above. It was confirmed that a breakage occurred at the tibia T. On the other hand, when the thickness is larger than 150 μm, the adhesion strength is less than 10 kg/cm$^2$. In this case, it was also confirmed that a breakage occurred in the porous lamination component S1.

This breakage occurrence is assumably explained as follows. When the above-mentioned thickness is in the range of 10 to 150 μm, the bone cells which penetrate the through holes H and grow therein are firmly anchored by the projection portions h of the thin sheets 1, 2, . . . projecting in the central direction of the through holes H as shown in the sectional view of FIG. 3. When the thickness is smaller than 10 μm, the amount of the projection at the projection portions h is too small and the bone cells are not sufficiently supported, thereby being incapable of firmly anchoring the bone cells. When the thickness is larger than 150 μm, the amount of the projection at the projection portions h is large, and the diameter of the through holes H in the direction of the thickness is reduced to about 10 μm, thereby assumably resulting in the breakage of the bone tissues at the region of the reduced diameter portions.

Furthermore, when the thickness is smaller than 10 μm, the number of the thin sheets 1, 2, . . . to be laminated increases significantly. This makes the production of the porous lamination component extremely difficult.

Next, still other samples of the porous lamination component S1 comprising thin sheets 1,2,... having the through holes alternately disposed as shown in FIG. 4 and also having different thickness values listed in Table 2 were made in accordance with the above-mentioned method. The shape of the through holes H in the porous lamination component S1 was hexagonal and its effective diameter was 300 μm and the volume porosity of the porous lamination component S1 was 60%. These samples of the porous lamination components S1 were subjected to the above-mentioned animal experiments and the adhesion strength values were measured after ten weeks. The measurement results are shown in Table 2.

TABLE 2

| Sample No. | Thickness of thin sheet (μm) | Adhesion strength (kg/cm$^2$) |
| --- | --- | --- |
| 7 | 5 | 9.5 |
| 8 | 10 | 12 |
| 9 | 50 | 12 |
| 10 | 100 | 12 |
| 11 | 150 | 12 |
| 12 | 175 | 9.9 |

As obviously indicated by Table 2, when the above-mentioned thickness is in the range of 10 to 150 μm, the adhesion strength is 12 kg/cm$^2$. This value is almost equal to the strength of the bone as described above. It was confirmed that a breakage occurred at the tibia T. On the other hand, when the thickness is smaller than 10 μm or larger than 150 μm, the adhesion strength is less than 10 kg/cm$^2$. In this case, it was confirmed that a breakage occurred in the porous lamination component S1.

Next, still other samples of the porous lamination component S1 comprising thin sheets 1,2, . . . having a thickness of 100 μm and also having the through holes H with different effective diameters listed in Table 3 were made in accordance with the above-mentioned method. The cross sectional structure of this porous lamination component S1 had the through holes H alternately disposed in the thin sheets 1, 2, . . . as shown in FIG. 4 and the volume porosity of the porous lamination component S1 was 60%. These samples of the porous lamination component S1 were subjected to the above-mentioned animal experiments and the adhesion strength values were measured after ten weeks. The measurement results are shown in Table 3.

TABLE 3

| Sample No. | Effective hole diameter (μm) | Adhesion strength (kg/cm$^2$) |
| --- | --- | --- |
| 13 | 50 | 7.2 |
| 14 | 75 | 8.7 |
| 15 | 100 | 12 |
| 16 | 200 | 12 |
| 17 | 300 | 12 |
| 18 | 400 | 12 |
| 19 | 500 | 9.3 |

As obviously indicated by Table 3, when the above-mentioned effective hole diameter is in the range of 100 to 400 μm, the adhesion strength is 12 kg/cm$^2$. This value is almost equal to the strength of the bone as described above. It was confirmed that a breakage occurred at the tibia T. On the other hand, when the diameter is smaller than 100 μm or larger than 400 μm, the adhesion strength is less than 10 kg/cm$^2$. In this case, it was confirmed that a breakage occurred in the porous lamination component S1.

Next, yet still other samples of the porous lamination component S1 comprising thin sheets 1,2, . . . having a thickness of 100 μm and the through holes H with an effective diameter of 300 μm and also having different volume porosity values listed in Table 4 were made in accordance with the above-mentioned method. The cross sectional structure of the porous lamination component S1 had the through holes H alternately disposed in the thin sheets 1,2, . . . as shown in FIG. 4.

TABLE 4

| Sample No. | Volume porosity (%) | Adhesion strength (kg/cm$^2$) |
| --- | --- | --- |
| 20 | 40 | 9.8 |
| 21 | 45 | 12 |
| 22 | 50 | 12 |
| 23 | 60 | 12 |
| 24 | 70 | 12 |

As obviously indicated by Table 4, when the above-mentioned volume porosity is more than 45%, the adhesion strength is 12 kg/cm$^2$. This value is almost equal to the strength of the bone as described above. It was confirmed that a breakage occurred at the tibia T. On the other hand, when the volume porosity is less than 45%, the adhesion strength is less than 10 kg/cm$^2$. In this case, it was confirmed that a breakage occurred in the porous lamination component.

Accordingly, it is found that the preferable thickness of the thin sheets 1, 2, . . . is 150 μm or less, more particularly in the range of 10 to 150 μm, the preferable effective hole diameter is in the range of 100 to 400 μm and the preferable volume porosity of the porous lamination component S1 is 45% or more.

Example 2

Figure 18:
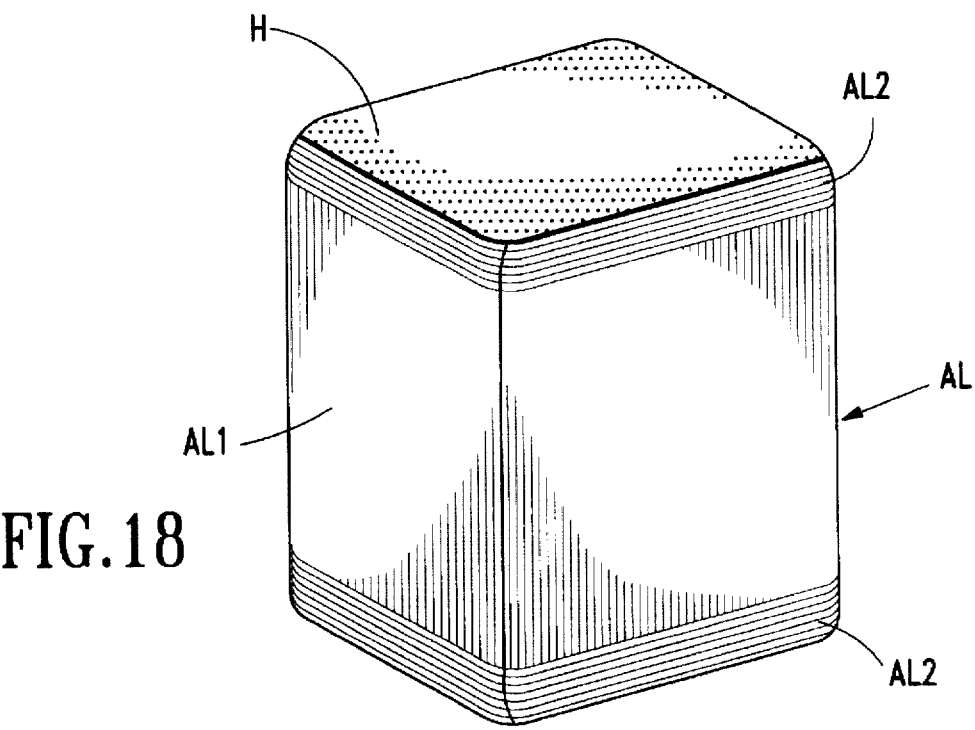
FIG. 18 is a perspective view illustrating an artificial vertebral body of the present invention.

FIG. 18 shows an artificial vertebral body AL used as a prosthesis of an example of the present invention. Ten pieces of 100 μm thick titanium thin sheets 1, 2, . . . having the same shape as that of the end surface of the artificial vertebral body AL were laminated to form a porous lamination component AL2 having a thickness of about 1 mm and this porous lamination component AL2 was bonded to both ends of the cubic artificial vertebral body AL made of a titanium alloy. The effective diameter of the through holes H was 300 μm. Other design items were the same as those of the example 1.

The artificial vertebral main body AL1 laminated with the porous lamination component AL2 comprising the lamination of the above-mentioned thin sheets 1,2, . . . as shown in FIG. 18 was heated up to about 900° C. in a vacuum furnace in an atmosphere of inert gas (argon). The surfaces of the artificial vertebral body AL were then coated with hydroxyapatite by flame spray coating. Next, the hydroxyapatite was converted into a paste state, and recrystallized by heat treatment. Bioglass ceramics was then used for coating.

In addition, to coat hydroxyapatite on the internal wall surfaces of the through holes H of the above-mentioned porous lamination component AL2, an artificial vertebral body AL was made as described below.

First, both ends of the artificial vertebral main body AL1 were coated with hydroxyapatite, and the porous lamination components AL2 were laminated on the artificial vertebral main body AL1 and then these laminated components were heated in the vacuum furnace as described above. Hydroxyapatite was coated only on the internal wall surfaces of the through holes H disposed close to the interfaces between the porous lamination components AL2 and the artificial vertebral main body AL1.

Furthermore, hydroxyapatite coating was performed by flame spray coating on one end of the porous lamination component AL2 which had been made previously in accordance with the method used for example 1. By heating the spray-coated surface abutted to the artificial vertebral main body AL1 in the vacuum furnace, an artificial vertebral body AL, in which the internal wall surfaces of the through holes H were coated with hydroxyapatite only on the intermediate layers of the porous lamination component AL2, was obtained.

In this way, the coating range in the cross section of the porous lamination component can be controlled.

Figure 19:
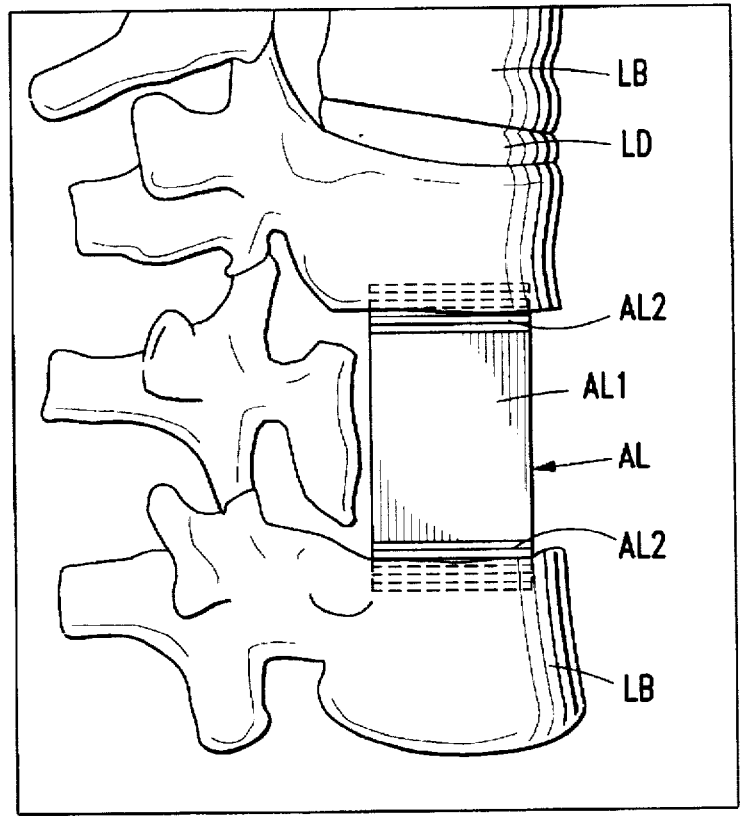
FIG. 19 is a side view illustrating a condition wherein the artificial vertebral body shown in FIG. 18 is inserted between intervertebral disks.

FIG. 19 is a side view illustrating the condition wherein a lumbar vertebra LB and an intervertebral disk LD are replaced with the above-mentioned artificial vertebral body AL.

In addition to the artificial vertebral body, this example can be applied to various prostheses such as spinous process spacers, iliac bone spacers, posterior cranial fossa plates and artificial knee joint tibial components.

Example 3

Figure 20:
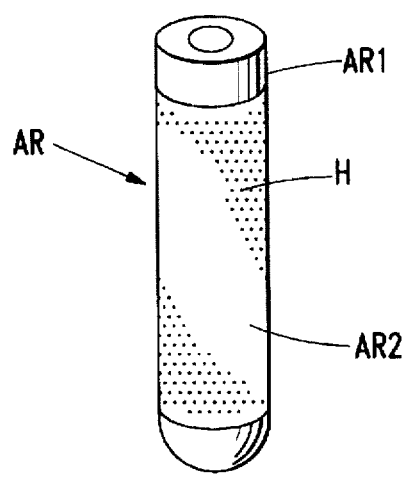
FIG. 20 is a perspective view illustrating an artificial dental root of the present invention.

FIG. 20 is a perspective view illustrating an artificial dental root AR of the present invention. The artificial dental root AR comprises a cylindrical artificial dental root body AR1 and an artificial dental root porous lamination component AR2 formed around the cylindrical surface of the artificial dental root body AR1.

Figure 21:
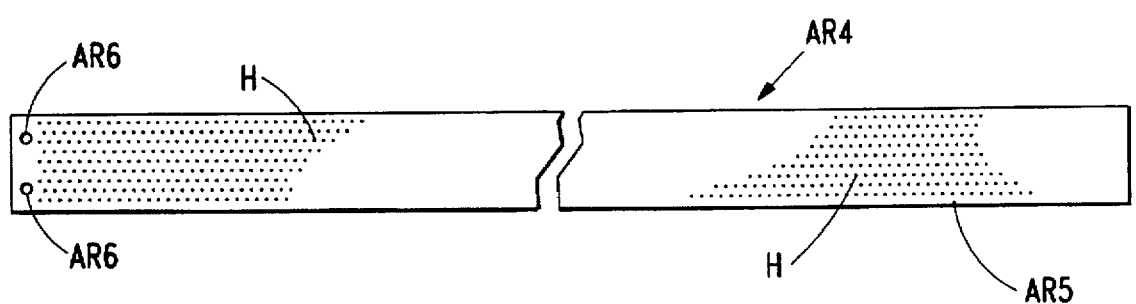
FIG. 21 is a top view illustrating the band-shaped thin sheet shown in FIG. 21.

FIG. 21 is a plan view of a thin sheet AR4 which is used to form the artificial dental root porous lamination component AR2. The thin sheet AR4 has a shape of band measuring 50 μm in thickness, 7.9 mm in width and 1000 mm in length. It has a plurality of through holes H with an effective diameter of about 300 μm, with non-pore fringe portions AR5 having a horizontal width of about 1 mm provided around the external fringe of the band. Furthermore, at the leading end of the above-mentioned thin sheet AR4, two fixture holes AR6 are provided.

Figure 22A:
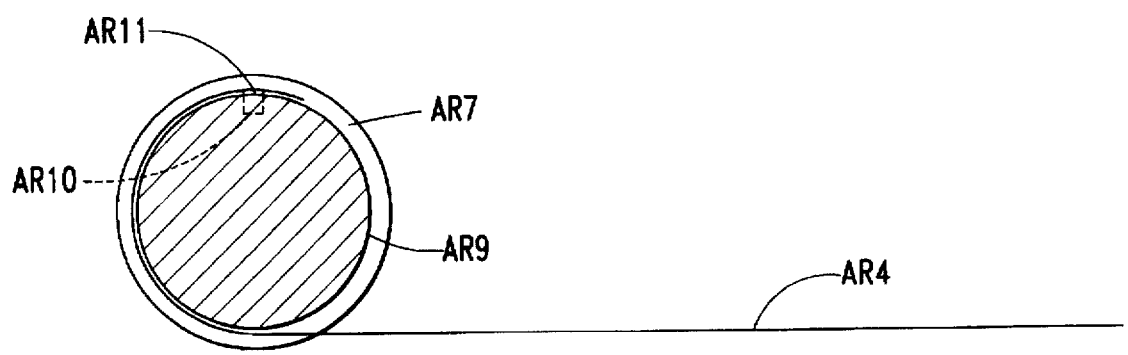
FIG. 22 is a sectional view illustrating a method of laminating the porous lamination component for the artificial dental root shown in FIG. 21.
Figure 22B:
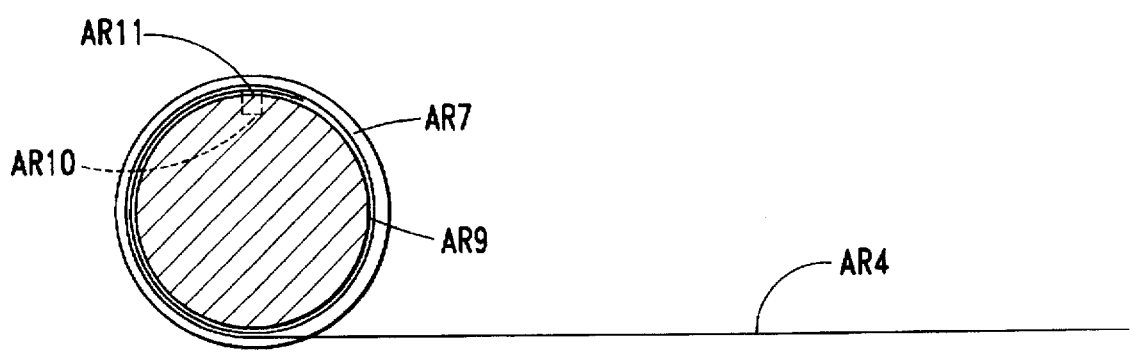

FIG. 22 is a sectional view illustrating a method of laminating the band-shaped artificial dental root porous lamination component AR2 over the porous lamination component accommodation section AR9 of the artificial dental root body AR1. The artificial dental root body AR1 was secured at the axial center thereof. Two 0.85 mm diameter titanium rods AR11 were respectively driven into the two thin sheet fixture holes AR10 disposed in the porous lamination component accommodation section AR9 of the artificial dental root body AR1 shown in FIG. 23. The above-mentioned fixture holes AR6 disposed in the thin sheet AR4 were fitted over the rods AR11. The projected portions of the rods AR11 were then removed by filing operation. After this, while the thin sheet AR4 was pulled to prevent it from being deflected, the artificial dental root body AR1 was rotated to wind the thin sheet AR4 around the artificial dental root body AR1.

Since the thickness of the thin sheet AR4 was 50 μm, the thickness of the artificial dental root porous lamination component AR2 was equal to the depth of the above-mentioned porous lamination component accommodation section, i.e., 1 mm after the thin sheet AR4 was rotated about 20 times. The thin sheet AR4 was then cut at an appropriate position, the trailing end thereof was temporarily secured by using adhesive and heated at about 900 C. in the vacuum furnace.

Figure 23:
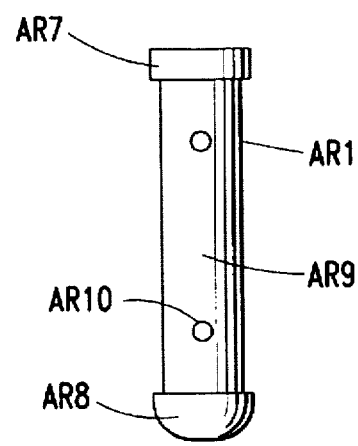
FIG. 23 is a side view illustrating the main body of the artificial dental root shown in FIG. 21.

FIG. 23 is a side view of the artificial dental root body AR1. The artificial dental root body AR1 is a cylinder with an overall length of 12 mm and comprises a 4 mm diameter end section AR7 disposed at one end thereof, a leading end section AR6 disposed at the other end thereof and having a round end, and the porous lamination component accommodation section AR9 disposed between the end section AR7 and the leading end section AR6 and having a length of about 8 mm and a diameter of 3 mm. The porous lamination component accommodation section AR9 is provided with two thin sheet fixture holes AR10 with a diameter of 0.8 mm in the porous lamination component accommodation section AR9.

It was possible to make the artificial dental root AR comprising the porous lamination component AR2 in the same way as described above by using the above-mentioned thin sheets AR4 having thickness values of 75, 100, 125 and 150 μm. When the thin sheet AR4 having a thickness of 175 μm was used, however, it had to be pulled strongly when it was wound around the circumference of the above-mentioned porous lamination component accommodation section AR9, resulting in breakage of the fixture holes AR6. To prevent this breakage, it was attempted to apply smaller tension force during the winding process. In this case, the thin sheet was not able to be wound accurately in accordance with the curvature of the porous lamination component accommodation section AR9. Even though an artificial dental root AR was obtained by winding the thin sheet AR4 in some way, only partial bonding was accomplished even when the artificial dental root AR was heated in the vacuum furnace. For this reason, no practical artificial dental root was able to be made.

According to the results of the actual practice, the thin sheets having thickness values in the range of 50 to 100 μm were able to be used most easily for the production of the artificial dental root AR.

Figure 24:
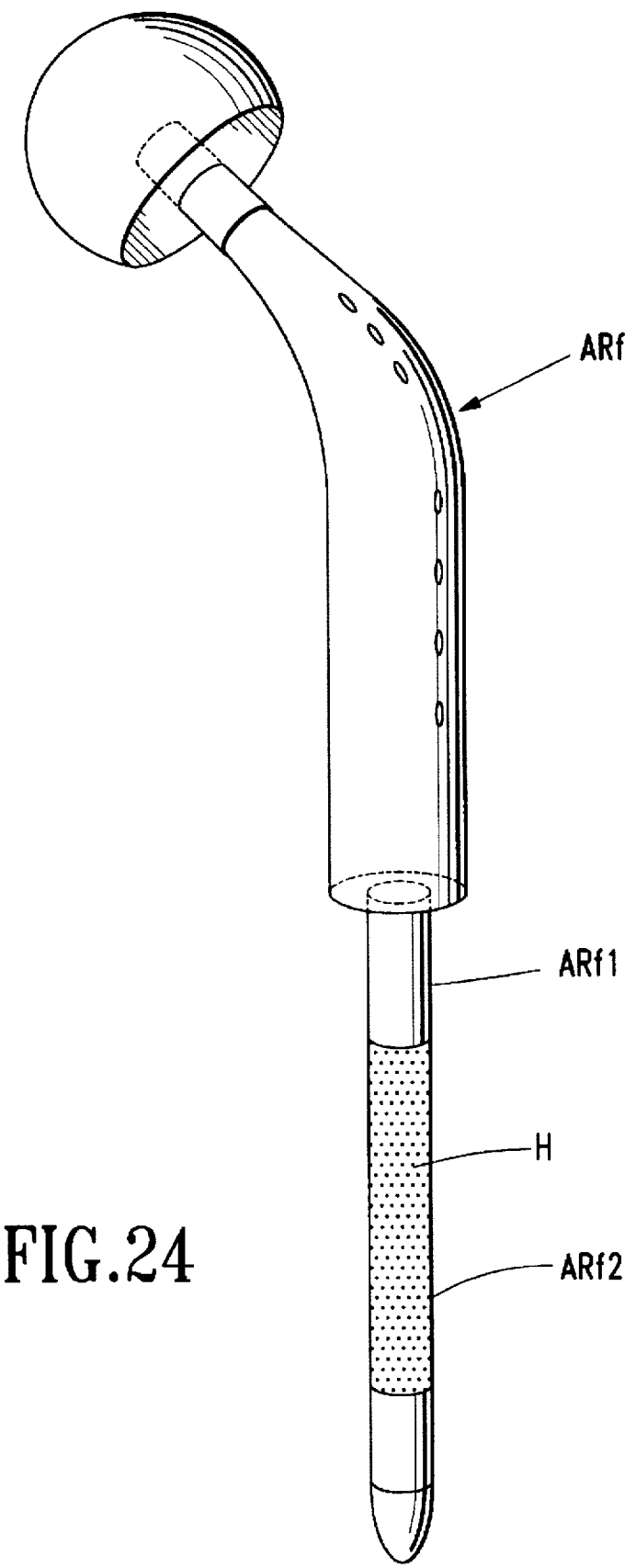
FIG. 24 is a perspective view illustrating a femoral prosthesis of the present invention.

The femoral prosthesis ARf shown in FIG. 24 has a porous lamination component ARf2 around the circumference of a bone embedding section ARf1. This porous lamination component can be formed by the same method as that used to make the porous lamination component AR2 of the above-mentioned artificial dental root AR, wherein the process of winding the thin sheet AR4 is included.

Figure 25:
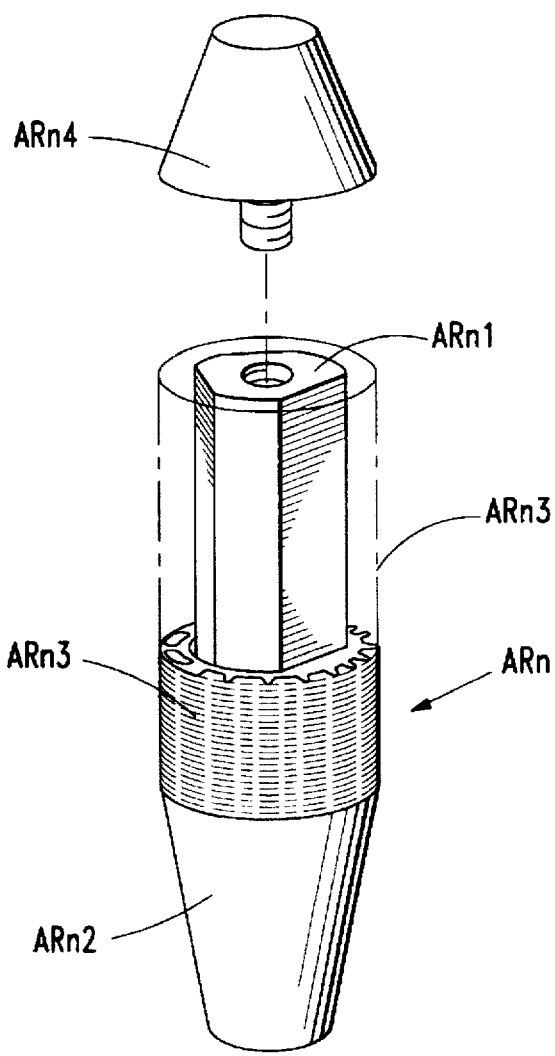
FIG. 25 is an exploded perspective view illustrating an example of an artificial dental root of the present invention.

FIG. 25 shows an artificial dental root ARn for the present example. This artificial dental root ARn comprises a main body section ARn2 provided with a hexagonal post section ARn1 having a smaller diameter, a substantially cylindrical porous lamination component ARn3 being fit over the post section ARn1 and a circular truncated cone being threadedly connected onto the above-mentioned post section ARn1.

Figure 26:
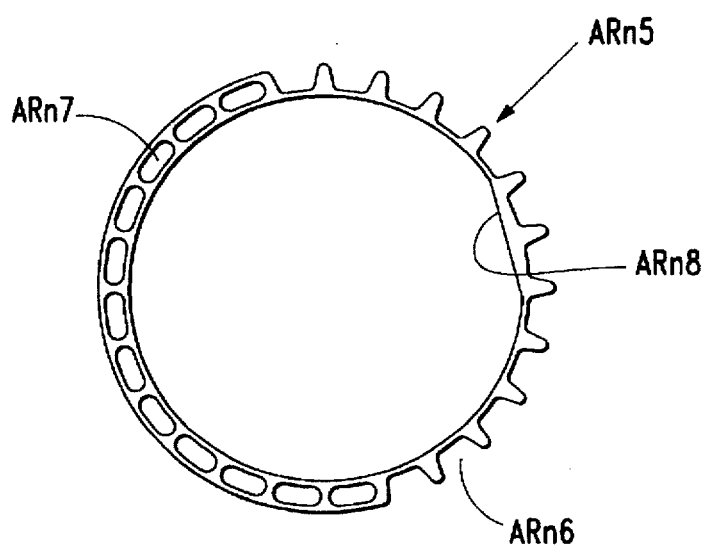
FIG. 26 is a plan view illustrating a thin sheet constituting the porous lamination component formed at the artificial dental root shown in FIG. 25.

The plan view of this example, FIG. 26, shows a loop-shaped thin sheet ARn5 used to constitute the above-mentioned porous lamination component ARn3. A plurality of externally open notches ARn6 are formed on one semi-circumferential section of the thin sheet ARn5 and a plurality of through holes ARn7 are formed on the other semi-circumferential section thereof. In addition, an internal straight side fringe ARn8 for preventing rotation is also formed on a part of the thin sheet ARn5 so that the straight side fringe mates with the external side surface of the above-mentioned post section ARn1.

To mutually adhere the above-mentioned thin sheets, the artificial dental root ARn can be heated in a vacuum furnace.

A plurality of the thin sheets ARn5 are laminated while they are displaced as desired in the vertical direction by using the internal straight side fringes ARn8 and the side surface of the above-mentioned post section ARn1, thereby forming the porous lamination component ARn3 having a porous cubic structure wherein the notches ARn6 and the through holes ARn7 of any vertically adjacent pair of the thin sheets ARn5 are vertically laminated.

With this structure, the bone tissues which have penetrated the side surface of the porous lamination component ARn3 through the notches ARn6 further penetrate the through holes ARn7 located above or below the notches, then grow in the porous cubic structure, thereby achieving a firmer connection between a bone and the artificial dental root ARn.

Example 4

Figure 27:
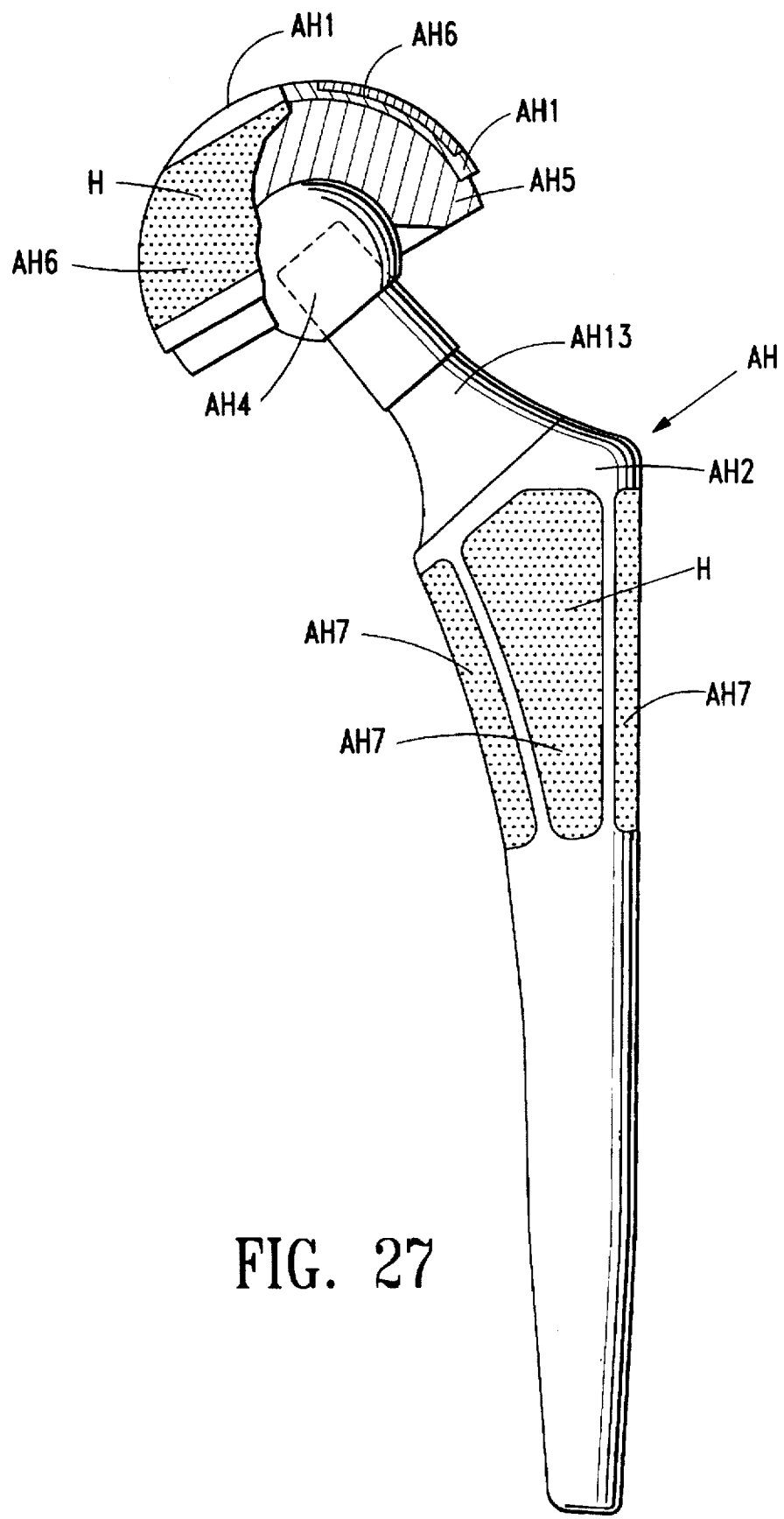
FIG. 27 is a side view of an artificial hip joint of the present invention.

FIG. 27 shows an artificial hip joint AH. This artificial hip joint AH comprises a hemispherical acetabular shell body AH1 to be secured to a pelvis, a rod-shaped femoral stem AH2 to be inserted into a femoral medullary cavity, a hemispherical ball member AH4 to be fit in the leading end of a rod-shaped member AH3 extending at about 45 degrees from one end of the femoral stem AH2 and a bearing member AH5 used to form a ball joint in combination with the ball member AH4 and inserted in the interior of the acetabular shell body AH1.

An acetabular porous lamination component AH6 and a femoral stem porous lamination component AH7 are formed on the surfaces of the acetabular shell body AH1 and the femoral stem AH2. The acetabular shell body AH1 and the femoral stem AH2 are made of a titanium alloy, and the acetabular porous lamination component AH6 and the femoral stem porous lamination component AH7 are made of pure titanium.

The acetabular porous lamination component AH6 is disposed in the greater part of the region where it directly contacts the pelvis. The femoral stemporous lamination component AH7 is formed mainly around the entire circumference in the proximal region of the femoral medullary cavity.

Figure 28:
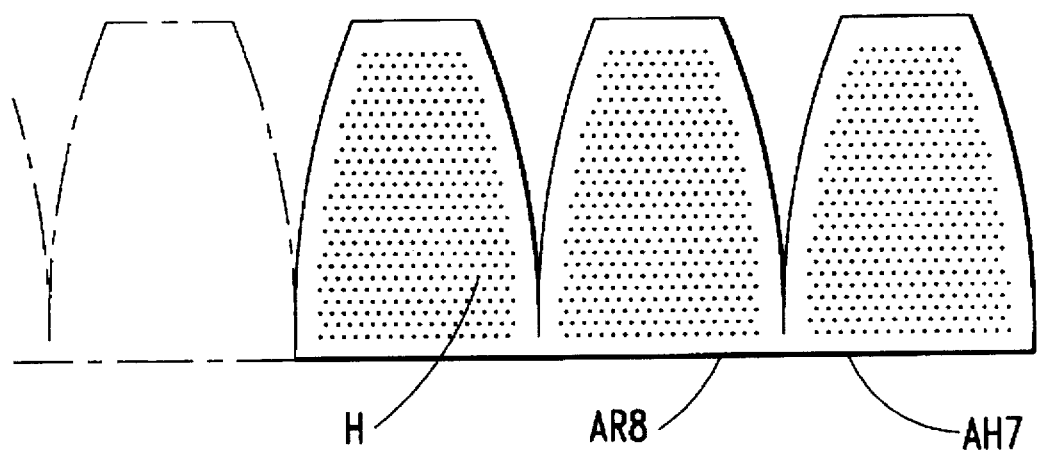
FIG. 28 is a plan view illustrating the thin sheet used to form an acetabular porous lamination component of the present invention.

FIG. 28 is a plan view of the thin sheet AH7 used to form the acetabular lamination component AH6. The thin sheet AH7 with a thickness of 100 μm has a non-pore fringe portion AH8 with a width of 1 mm around the entire circumference thereof and is provided with a plurality of through holes H with an effective diameter of about 300 μm in the other sections. The thin sheet AH7 has a shape comprising several pieces of roughly isosceles triangular forms arranged continuously along the extension line of the base sides of the triangular forms, wherein each triangular form is made by respectively connecting the ends of the base side with the ends of the top side (shorter than the base side) of each fragmental section of the thin sheet using curved lines. The shape of the thin sheet AH7 is almost equal to the shape obtained by unfolding a spherical surface.

Figure 29:
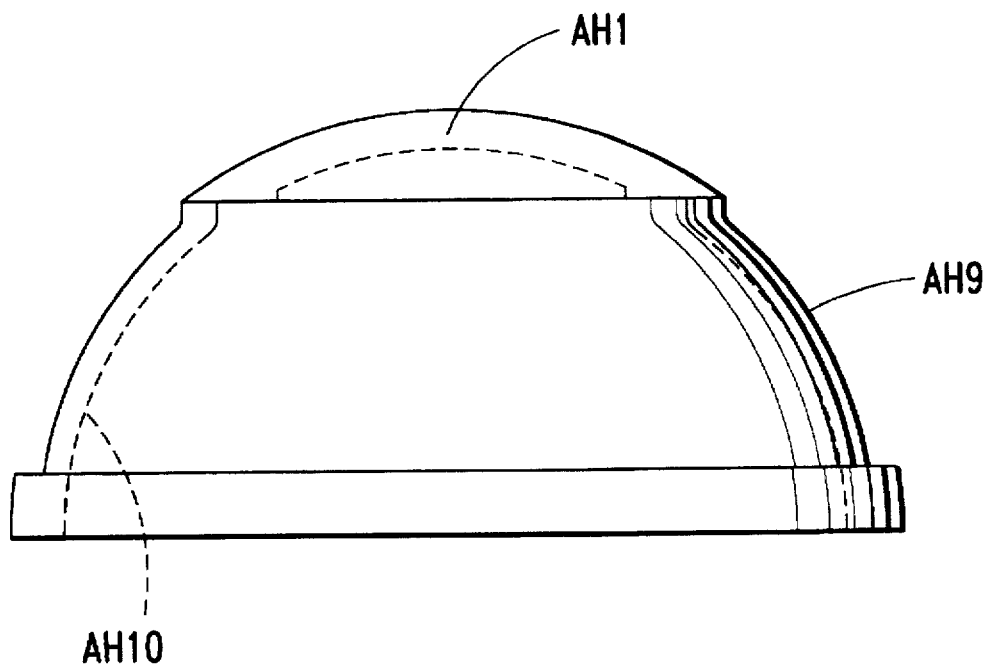
FIG. 29 is a side view of the acetabular shell body shown in FIG. 28.

FIG. 29 is a side view illustrating only the above-mentioned acetabular shell body AH1. The acetabular shell body AH1 is roughly a hemisphere with a diameter of 50 mm. From the position 5 mm away from the end surface of the acetabular shell body AH1, an acetabular porous lamination component accommodation section AH9 having a spherical surface with a diameter of 48 mm is formed coaxially with the acetabular shell body AH1. The top end of the accommodation section AH9 is positioned 5 mm below the vertex of the acetabular shell body AH1. In the interior of the accommodation section AH9, an internal ball with a diameter of 45 mm is included, which contacts the bearing member AH5.

Figure 30:
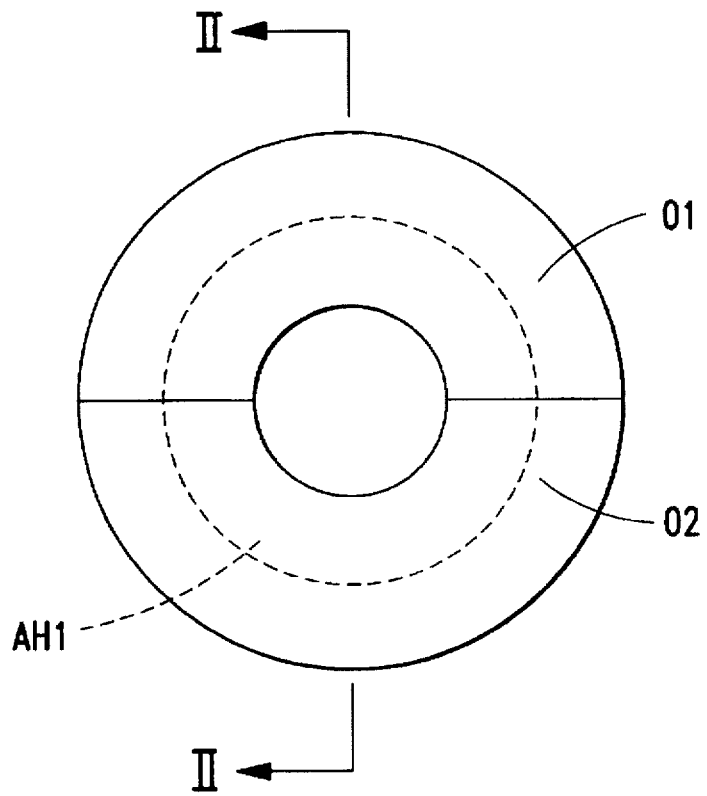
FIG. 30 is a view illustrating a condition wherein an acetabular porous lamination component shown in FIG. 28 is formed.

FIG. 30 shows a condition wherein the acetabular lamination component AH6 is formed on the acetabular porous lamination component accommodation section AH9 of the acetabular shell body AH1.

Figure 31:
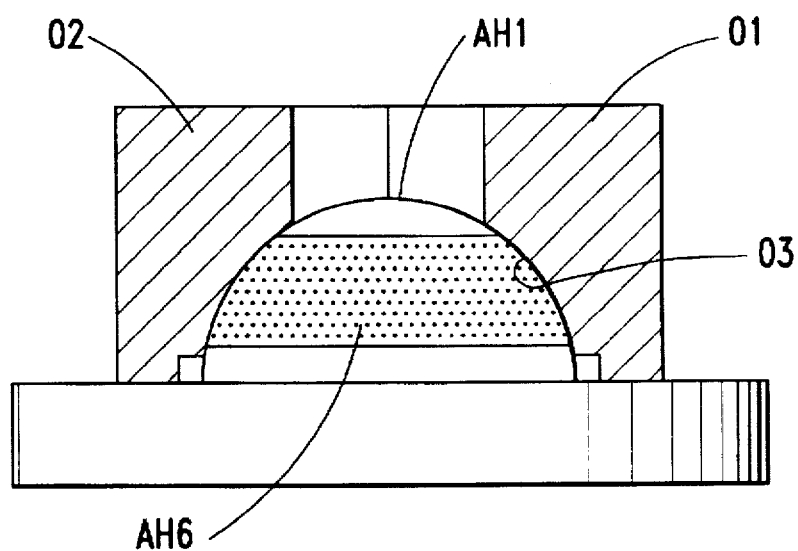
FIG. 31 is a sectional view taken on line II—II of FIG. 30.

The acetabular shell body AH1 is enclosed by metal molds 01 and 02. FIG. 31 is a sectional view taken on line II—II of FIG. 30. The metal molds 01 and 02 have an external shape obtained by dividing a cylinder measuring 70 mm in outer diameter and 50 mm in height into two pieces on the flat plane including the central axis of the cylinder. Inside the molds, a hemispheric bore 03 with a diameter of 50.5 mm is provided to allow the thin sheet AH7 to be formed around the entire circumference of the acetabular porous lamination component accommodation section AH9. When the acetabular shell body AH1 and ten pieces of the thin sheets AH7 are inserted in the metal molds 01 and 02 provided as described above, and the metal molds are made contact with each other at their division surfaces, the thin sheets AH7 are deformed into a hemispheric form inside the acetabular porous lamination component accommodation section AH9. To make the metal molds 01 and 02 contact with each other, screws can be used to pull the molds. The thin sheets AH6 can also be bent by pressing them against a cylindrical shaft with a diameter of 50 mm beforehand. By heating the thin sheets AH7 to about 900° C. in the vacuum furnace, the acetabular porous lamination component accommodation section AH9 is bonded to the surface of the acetabular shell body AH1. To form a hemispherical porous lamination component, it is not always necessary to use hemispherical surfaces such as those provided in the metal molds 01 and 02, the object for obtaining a hemispherical surface can be attained by partially supporting the thin sheets at about three points.

Figure 32:
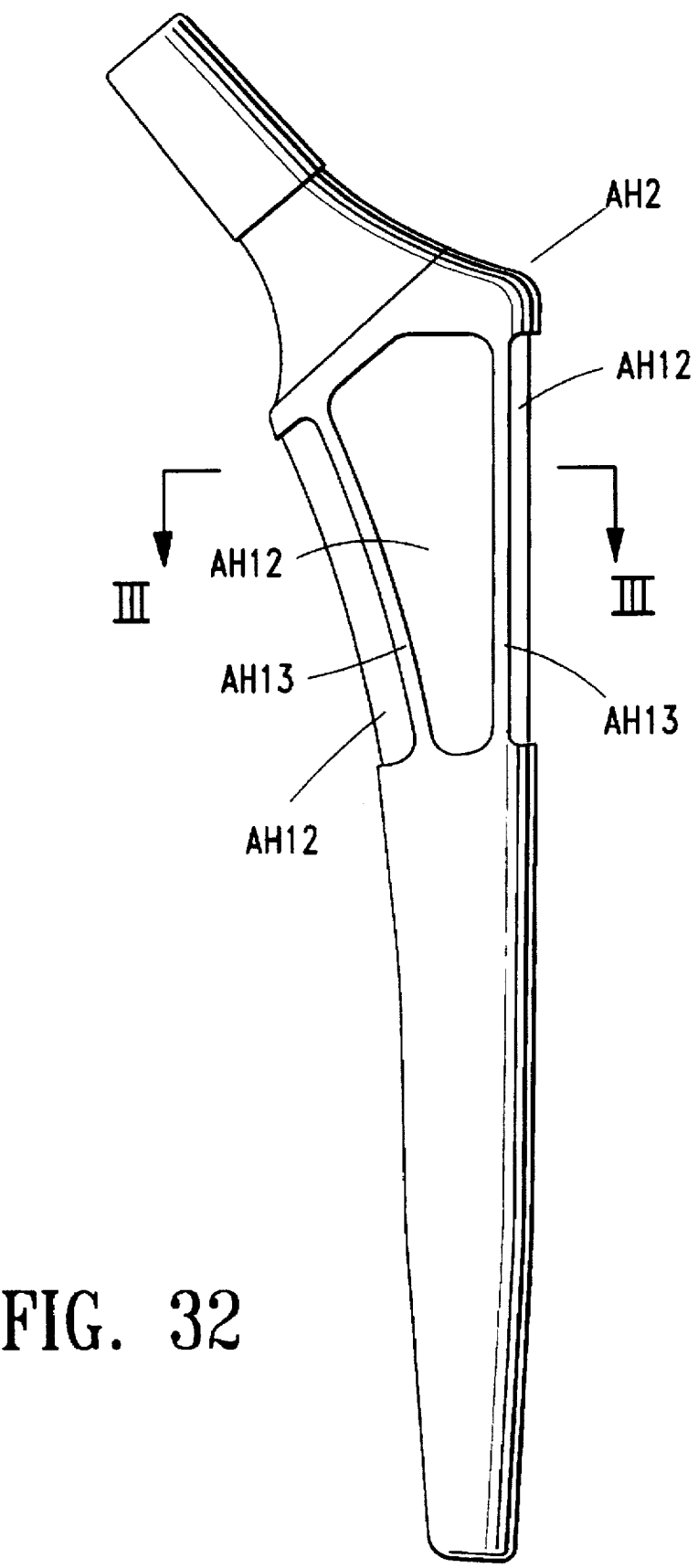
FIG. 32 is a side view of a femoral stem of the present invention.

FIG. 32 is a side view of the femoral stem AH2. In the middle section of the femoral stem AH2, a femoral stem porous lamination component accommodation section AH12 is provided around the entire circumference of the stem AH2 in a width of about 60 mm. The femoral stem porous lamination component accommodation section AH12 comprises two flat surfaces and two curved surfaces, and these surfaces are partitioned by bank-shaped projections AH13.

Figure 33:
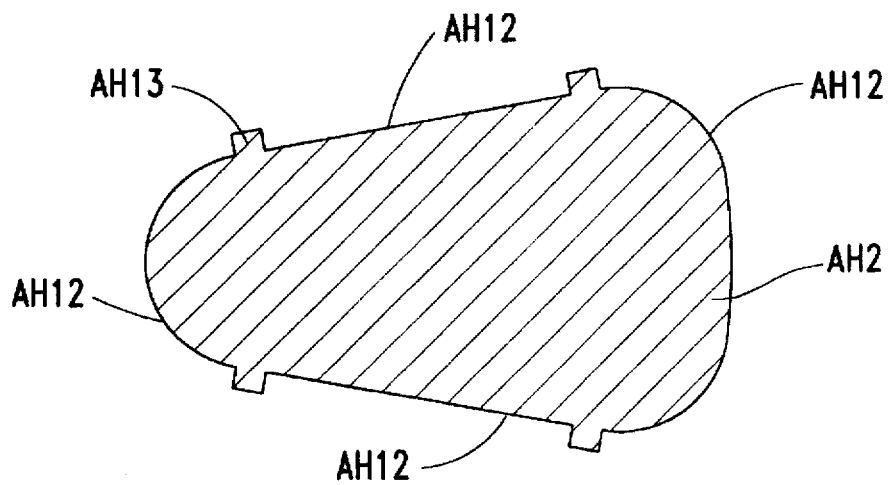
FIG. 33 is a sectional view taken on line III—III of FIG. 32.

FIG. 33 is a sectional view taken on line III—III of FIG. 32. The cross section is symmetrical and comprises flat surfaces with a width of about 18 mm, curved surfaces with radius curvatures of 6 and 25 mm and widths of 10 and 14 mm, and the bank-shaped projections AH13 used to partition the surfaces.

Figure 34:
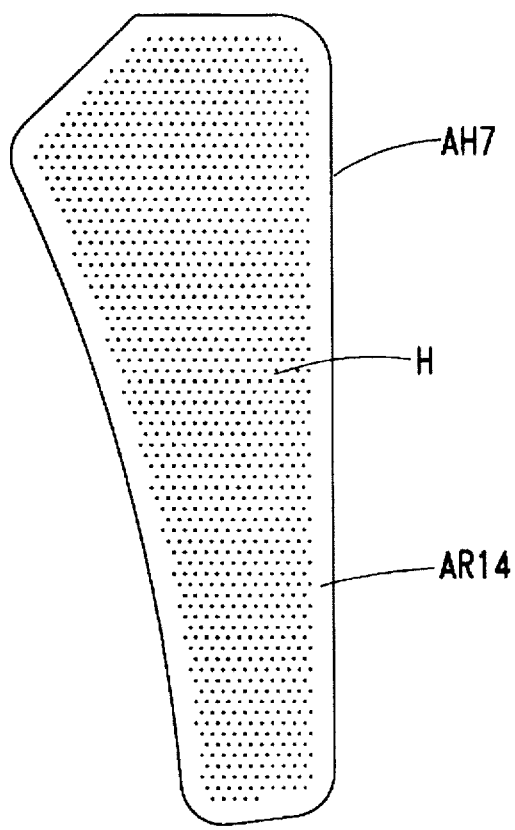
FIG. 34 is a plan view illustrating a thin sheet composing the porous lamination component for a femoral stem of the present invention.

FIG. 34 is a plan view of the thin sheet AH7. The size of the external shape thereof is slightly smaller than that of the femoral stem porous lamination component accommodation section AH12. The thin sheet AH7 has a thickness of 100 μm and is provided with non-pore fringe portion AH14 with a width of about 1 mm around the entire circumference of the thin sheet AH7. In the other sections of the thin sheet AH7, a plurality of through holes H with an effective diameter of about 300 μm are provided.

Figure 35:
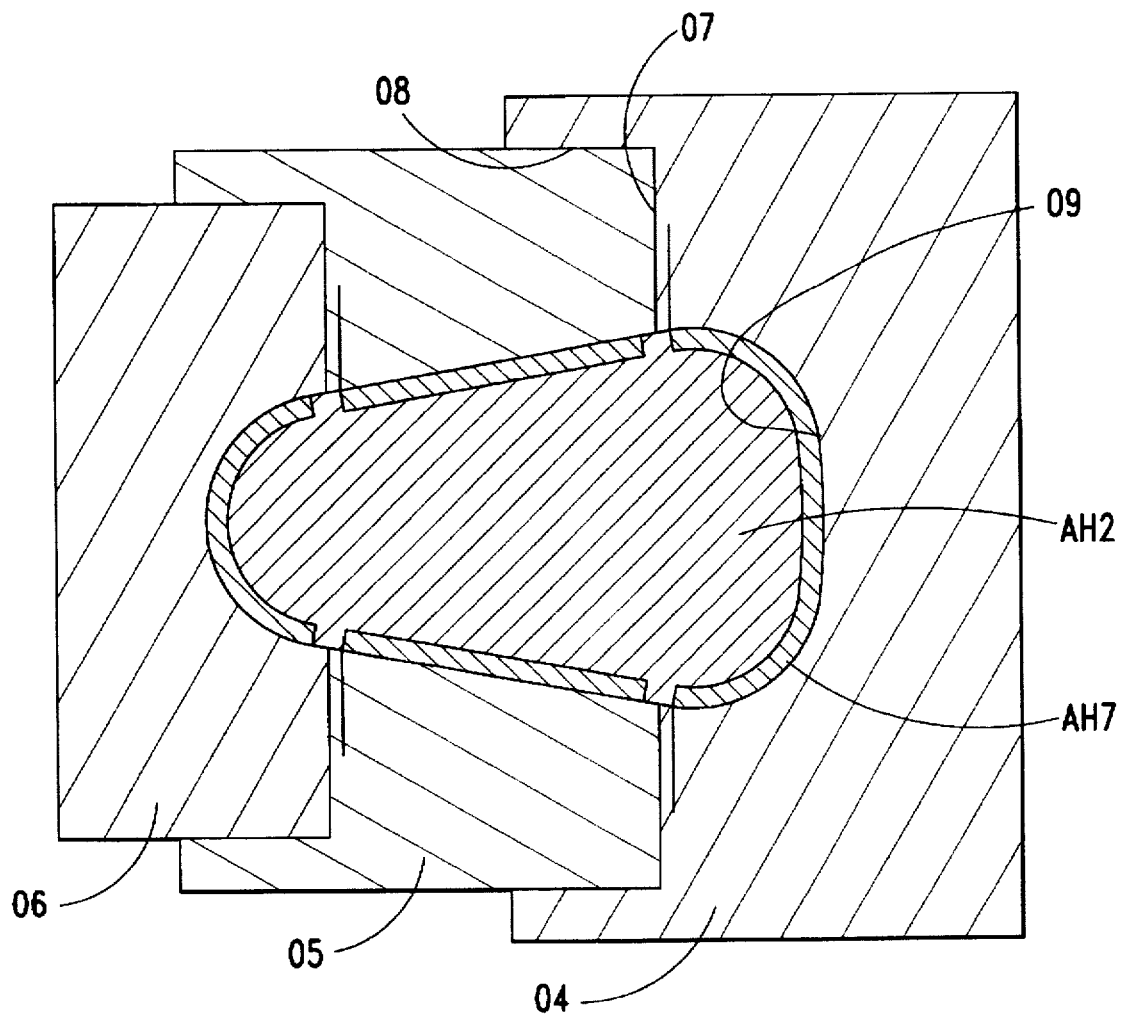
FIG. 35 is a view illustrating a condition wherein the porous lamination component for a femoral stem of the present invention is formed.

FIG. 35 shows a condition wherein a femoral stemporous lamination component AH16 is formed in the femoral stem AH2. Metal molds 04, 05 and 06 respectively correspond to the corresponding sections of the femoral stem porous lamination component accommodation section AH12. A form setting surface 09 is provided to form ten layers of the thin sheets AH7. Furthermore, stop surfaces 07 and 08 are provided so that the metal molds 04, 05 and 06 can be secured at the predetermined positions. When the metal molds are put in the vacuum furnace and heated at 900° C., the femoral stem porous lamination component AH16 can be formed in the femoral stem AH2. The porous lamination component AH16 can also be formed as described below. After a lamination component comprising thin sheets is heated to have a porous condition, it is cut by laser processing so that it can fit in the femoral stem porous lamination component accommodation section AH12, then it is formed by using the above-mentioned metal molds, thereby obtaining the porous lamination component AH16. When the porous lamination component is formed to have a curved surface, it can be bent beforehand in accordance with the curvature of the surface.

Figure 36:
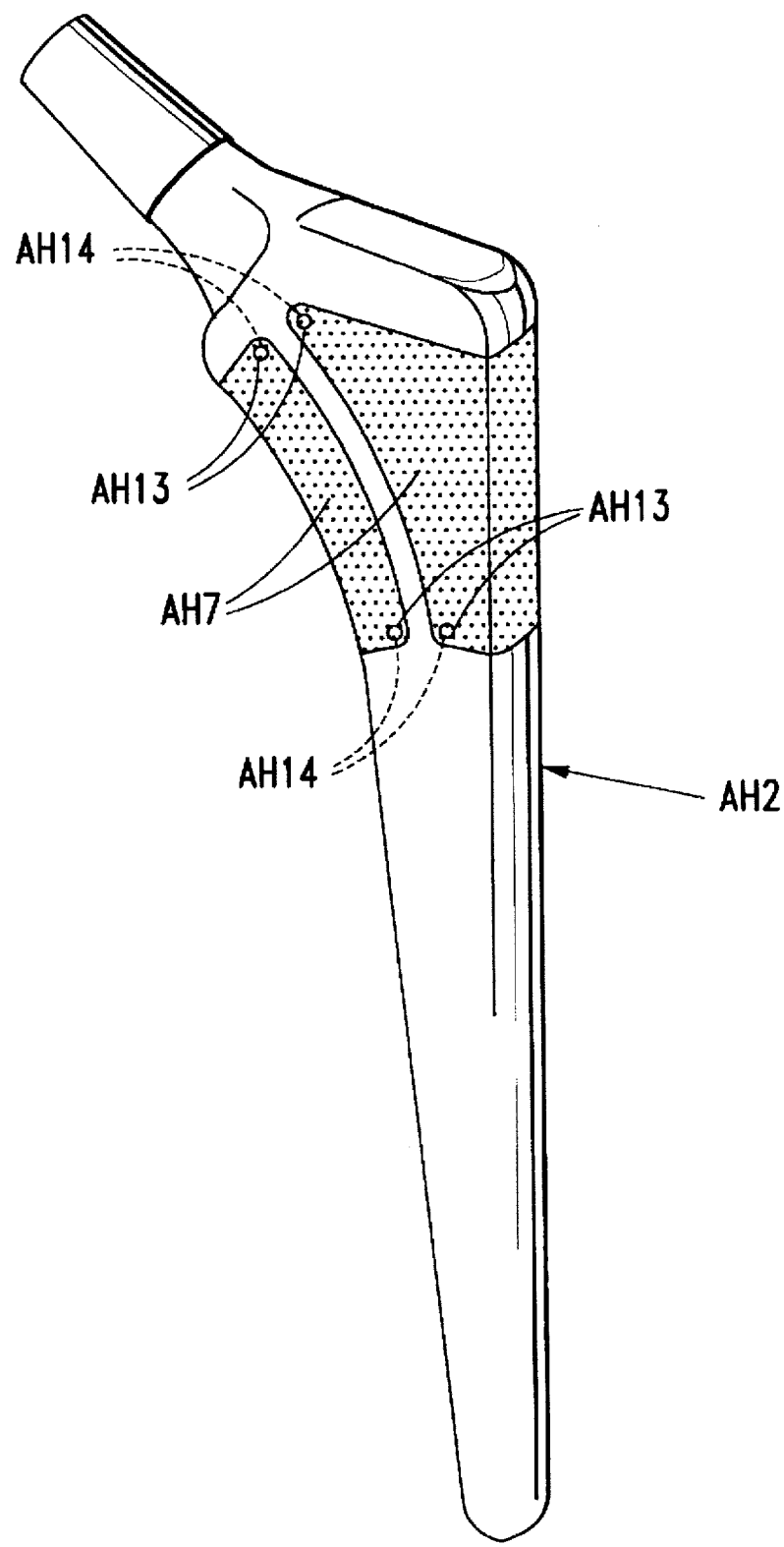
FIG. 36 is a perspective view illustrating an example of an artificial coxa of the present invention.
Figure 37:
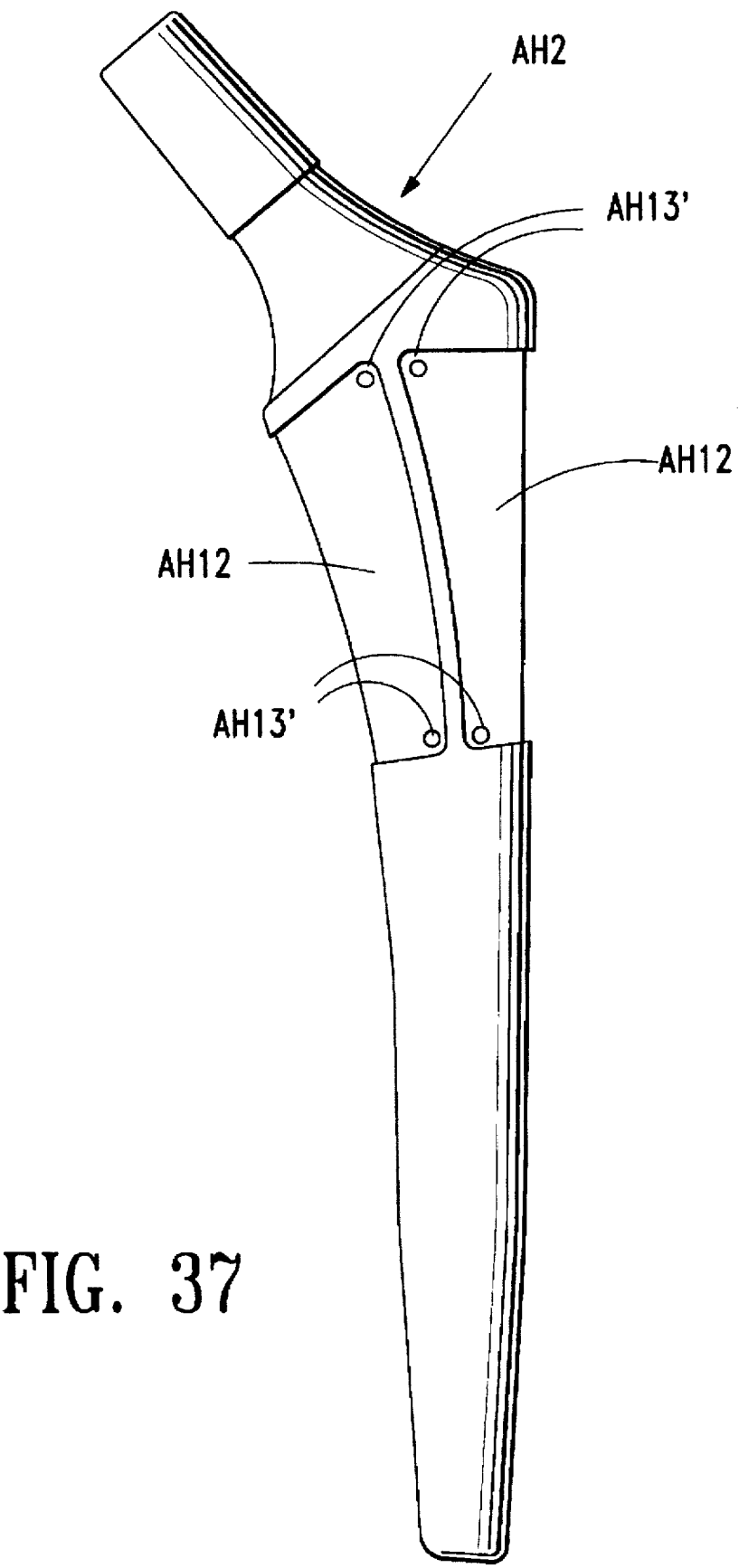
FIG. 37 is a side view illustrating a stem body constituting the stem shown in FIG. 36.

FIG. 36 shows another embodiment of the stem AH2 used to constitute the artificial coxa AH for this example. This example uses fixture elements AH13, such as rivets or anchor bolts, as means for securing the porous lamination components AH7. To accomplish this securing method, fixture holes AH14 are formed in porous lamination component receiving sections AH12 of the stem AH2.

Figure 38:
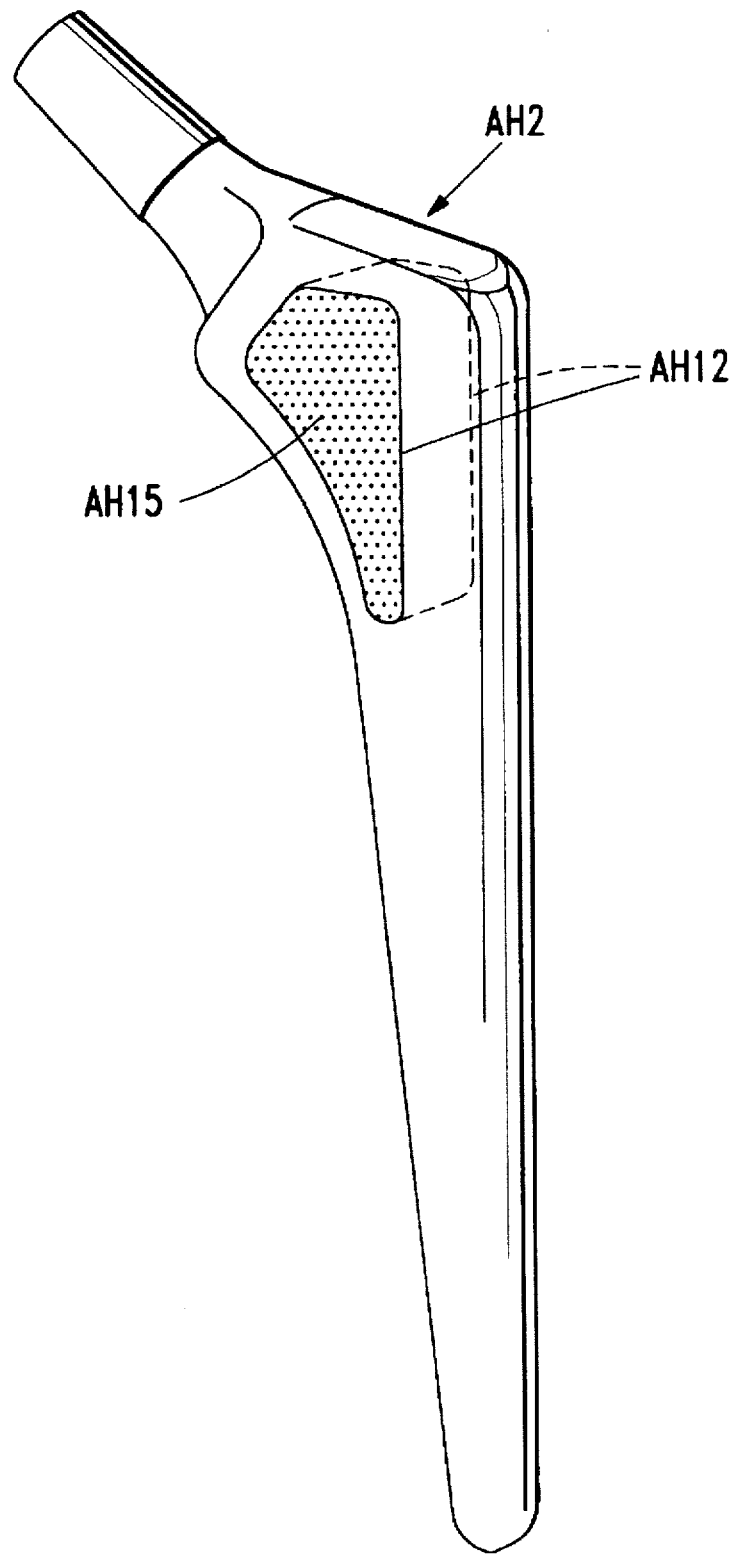
FIG. 38 is a perspective view illustrating the stem constituting an example of the artificial coxa of the present invention.
Figure 39:
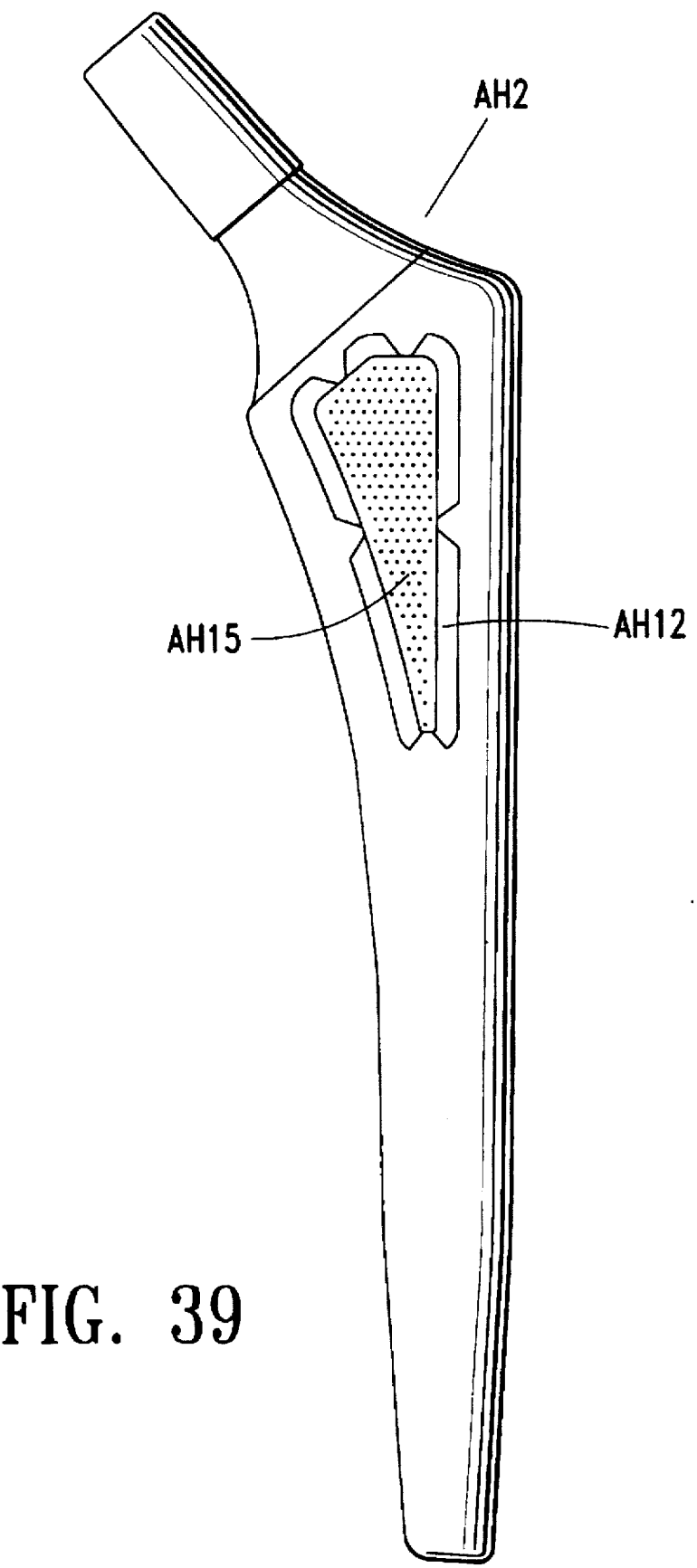
FIG. 39 is a side view illustrating the stem constituting an example of the artificial coxa of the present invention.
Figure 40:
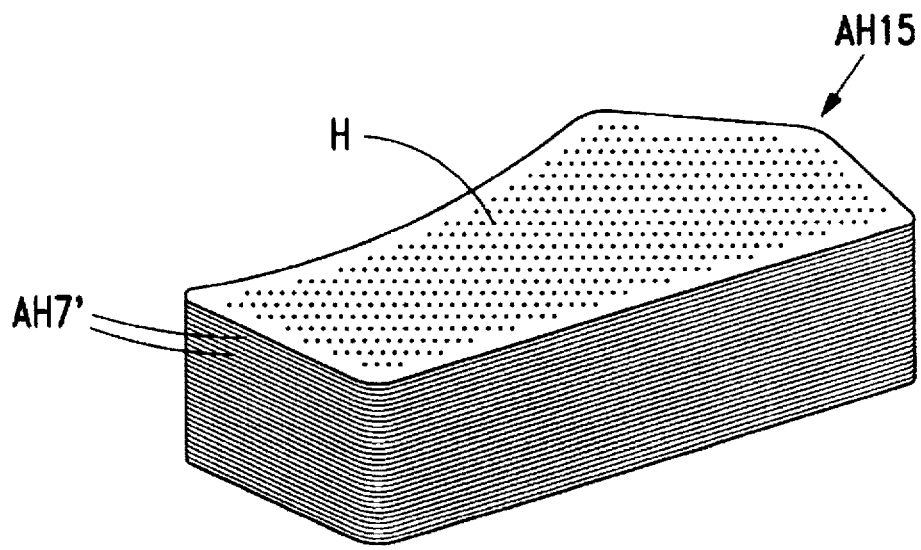
FIG. 40 is a perspective view illustrating the porous lamination component constituting the stem shown in FIG. 38 or FIG. 39.
Figure 41:
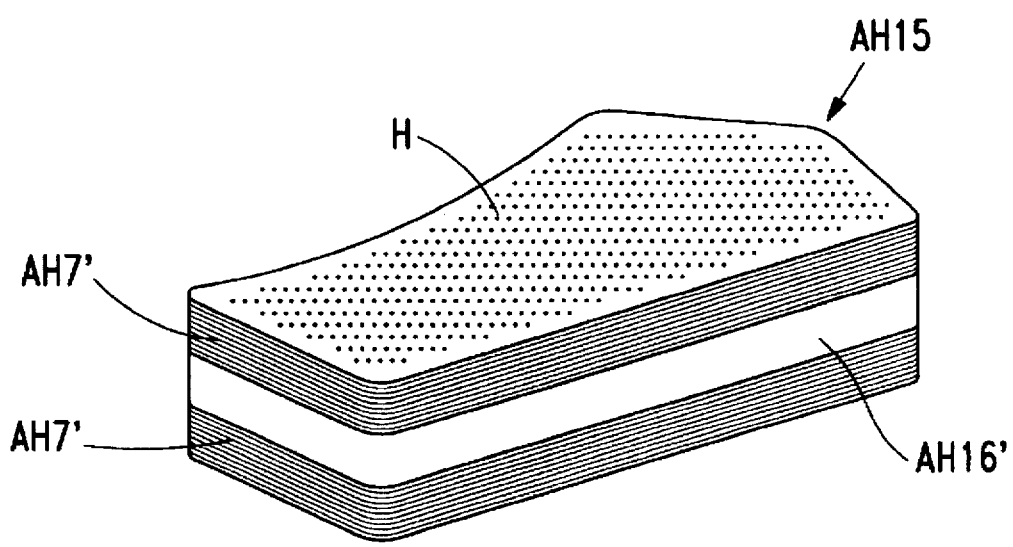
FIG. 41 is a perspective view illustrating the porous lamination component constituting the stem shown in FIG. 38 or FIG. 39.

In addition, FIGS. 38 and 39 show still other embodiments of the stem AH2. Porous lamination component AH15 which is made by laminating a plurality of thin sheets AH7' (FIG. 34) in the porous lamination component receiving section AH12 which is a through hole disposed at and horizontally passing through the intermediate section of the stem AH2 as shown in FIG. 40, or by fitting and securing a porous lamination component AH15 comprising thin sheets AH7' being laminated on both sides of a metallic intermediate member AH16 as shown in FIG. 41. It should be noted that the porous lamination component AH15 of the stem AH2 shown in FIG. 39 are different from those shown in FIG. 40 in their plan-view shapes.

Example 5

Figure 42:
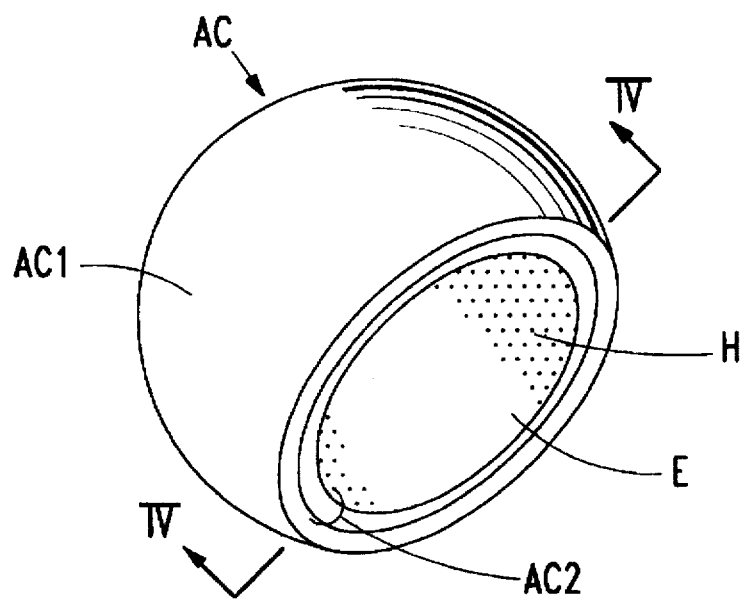
FIG. 42 is a perspective view illustrating a femoral head cup of the present invention.

FIG. 42 is a perspective view of a femoral headcup AC of the present invention. The femoral headcup AC is a hemisphere with a diameter of 38 to 60 mm. It comprises a 2 mm thick sliding component AC1 made of PVA (polyvinyl alcohol) on the outside thereof and a 2 mm thick porous lamination component AC2 having a three-layer structure described below on the inside thereof. Accordingly, the cup has a thickness of 4 mm and functions as a sliding member used to slide with the acetabulum after the cup is replaced with the femoral head.

Figure 43:
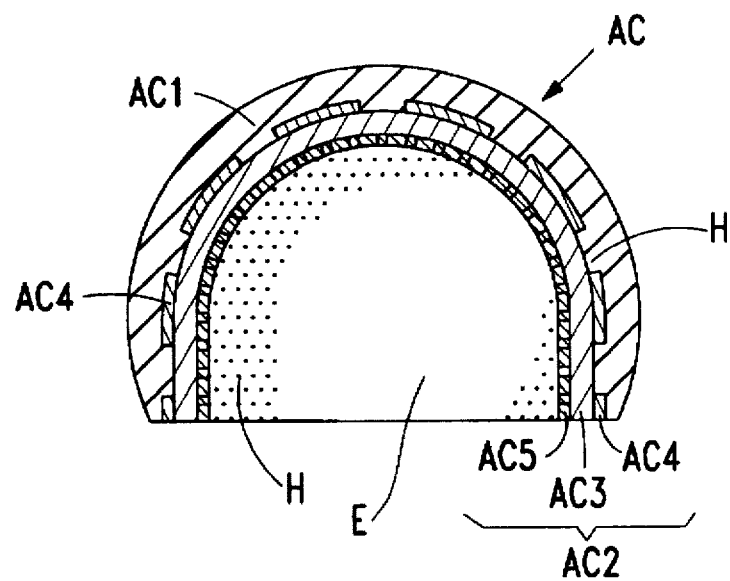
FIG. 43 is a sectional view taken on line IV—IV of FIG. 42.

FIG. 43 is a sectional view taken on line IV—IV of FIG. 42. The above-mentioned porous lamination component AC2 has a three-layer structure comprising a PVA joint section AC4 having through holes H with an effective diameter of about 3 mm and being filled with PVA on the entire surface thereof and made by laminating five pieces of 100 μm thick pure titanium sheets, a bone contacting section AC5 having through holes H with an effective diameter of 300 μm on the entire surface thereof on the side of internal space E and made by laminating ten pieces of 50 μm thick pure titanium sheets, and a 1 mm thick cup component AC3 having no through holes, made of pure titanium and intervened between the PVA joint AC4 and the bone contacting section AC5.

Next, the method of making the above-mentioned femoral head cup AC is described below. First, thin sheets, each having through holes H with an effective diameter of 300 μm and a thickness of 50 μm, and other thin sheets, each having through holes H with an effective diameter of 3 mm and a thickness of 100 μm, were made by using the spherical surface unfolding method described for the example 4. Five pieces of the former thin sheets and five pieces of the latter thin sheets were laminated on both sides of the above-mentioned cup component AC3. These were temporarily secured and put into a metal mold (not shown). The metal mold was then put into the vacuum furnace and heated at about 900° C. so that they were bonded. In this way, the above-mentioned porous lamination component AC2 was made.

Next, an appropriate amount of an adjusted PVA solution was poured into a metal mold (not shown). The above-mentioned porous lamination component AC2 was then placed on the mold, with the side of the internal space E facing upward. The metal mold and the porous lamination component AC2 were cooled for a while so as to fix PVA around the porous lamination component AC2, then put into silicone oil at 140° C. for heat treatment to form the sliding component AC1 comprising PVA gel having a low water content on the outside of the porous lamination component AC2, thereby obtaining the above-mentioned femoral headcup AC.

The above-mentioned PVA solution was adjusted in accordance with the method disclosed by Japanese Laid-open Patent Application No. 2-86606 and No. 3-141957 by adding 10 g of PVA having a polymerization degree of 5000 and a saponification degree of 99.9 mol % to a dimethylsulfoxide/water mixture solvent and by stirring the ingredients at 130° C. for two hours to dissolve them.

Figure 44:
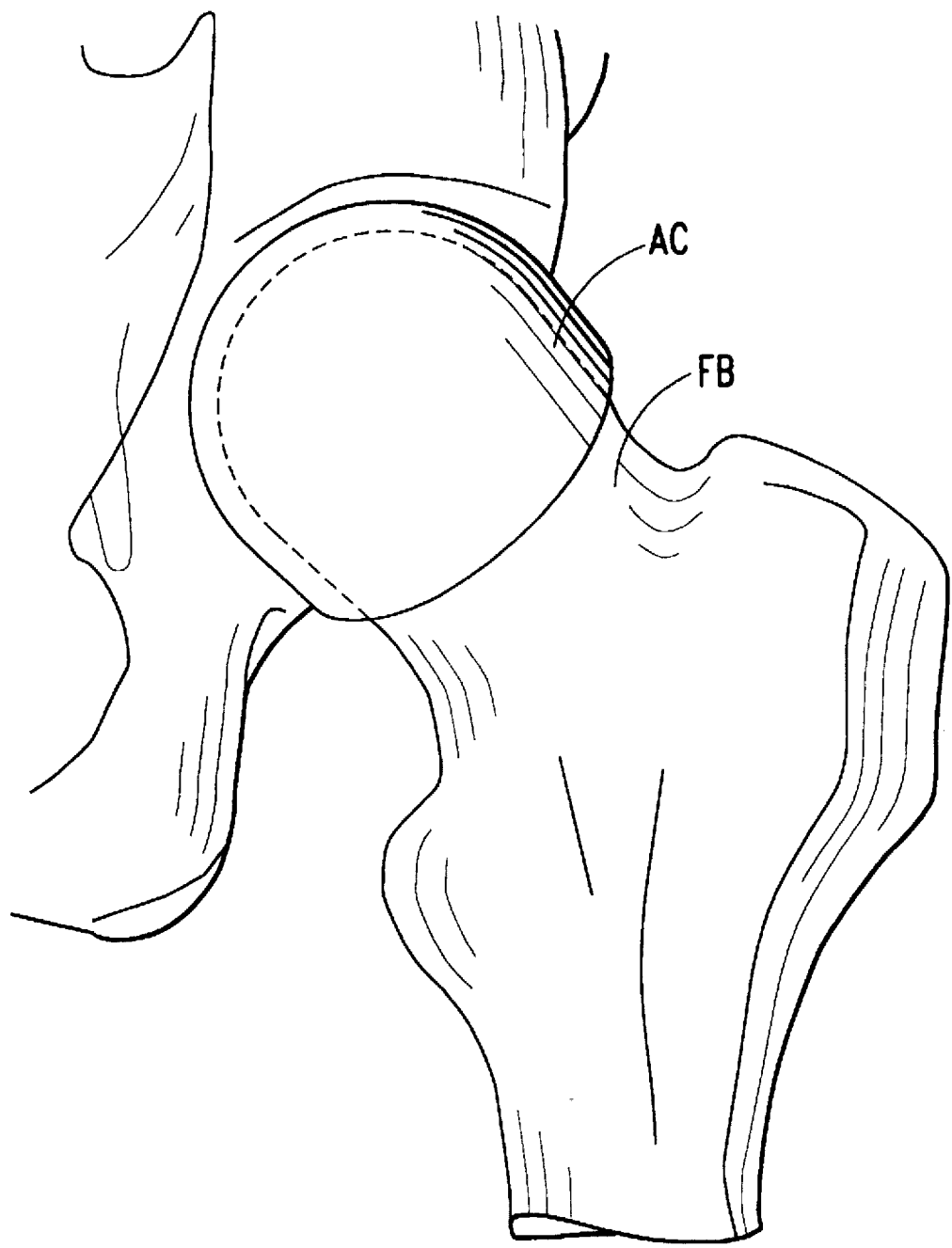
FIG. 44 is a perspective view illustrating a condition wherein a femoral bone is replaced with a femoral head cup of the present invention.

FIG. 44 shows a condition wherein the femoral head cup AC is fitted on the femoral bone FB.

As described above, the porous lamination components used to coat the surfaces of the prostheses can be integrated with not only the above-mentioned PVA but also organic materials such as super high molecular polyethylene or silicone to be used for the sliding section members, impact load absorbing members or elastic deformation members of prostheses. The porous lamination components are, therefore, superior in enhancing the strength of the members made of organic materials and in joining the organic material members to bone tissues with which the organic material members make contact.

Example 6

Figure 45:
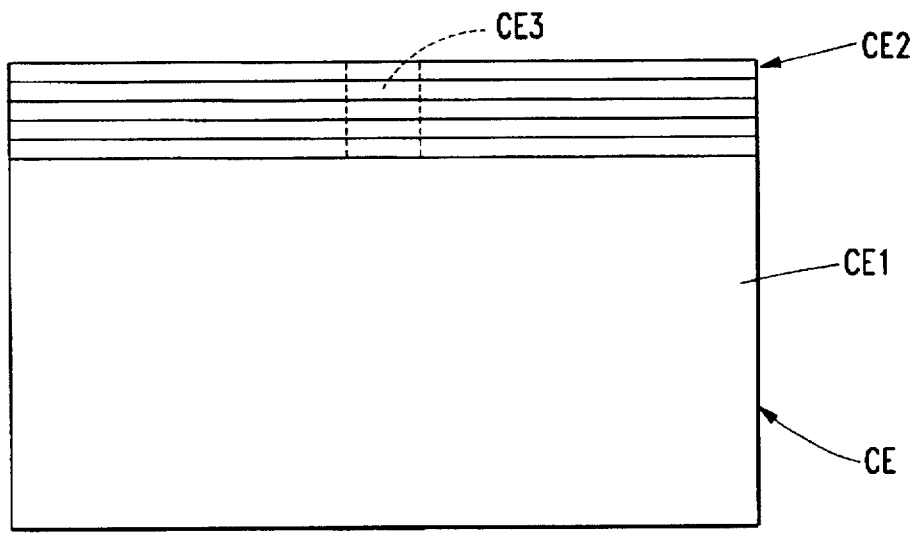
FIG. 45 is a perspective view illustrating an artificial vertebral body of the present invention.

FIG. 45 is a side view of an artificial vertebral body CE used as a prosthesis of the present invention. The main body CE1 of this artificial vertebral body is a cubic component made of alumina ceramics, measuring 10×10×5 mm. On the end surface thereof, a porous lamination component CE2 having a thickness of 1 mm and made of titanium is integrated with the main body CE1. The porous lamination component CE2 comprises ten laminated thin sheets, each having a thickness of 100 μm.

Figure 46:
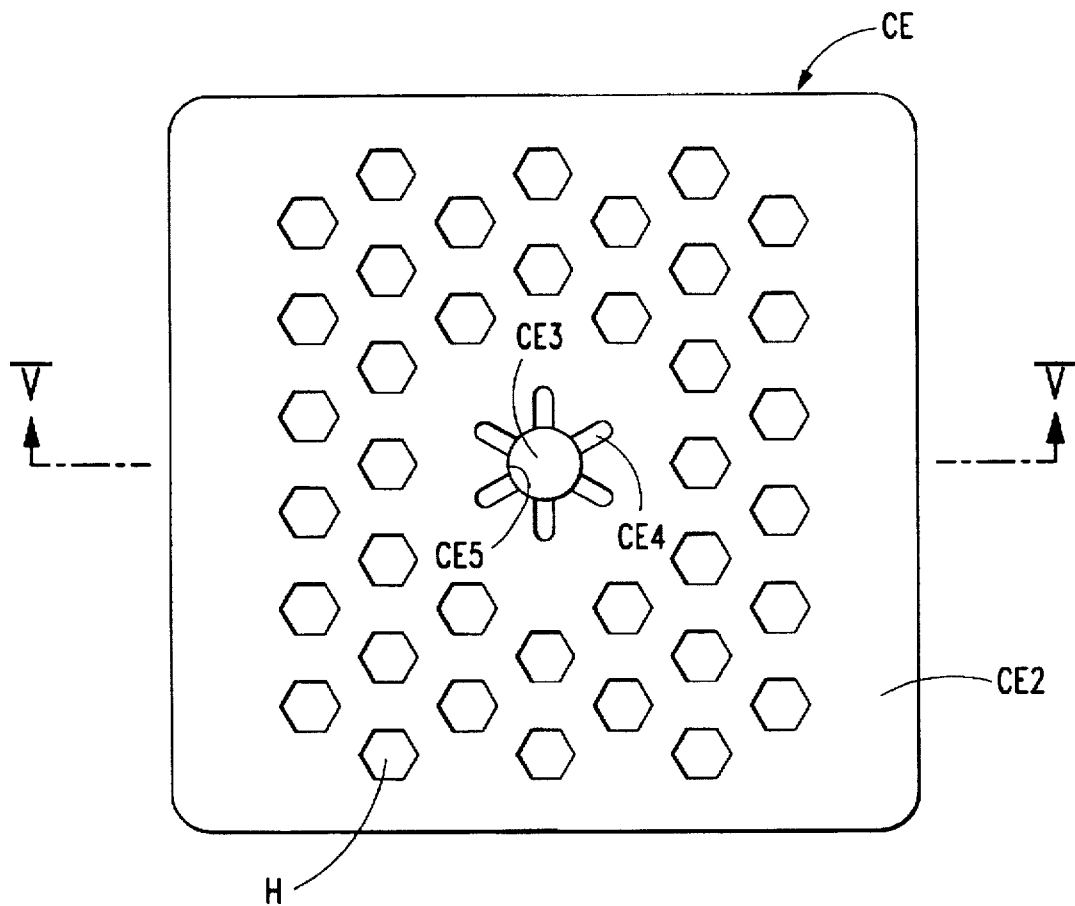
FIG. 46 is a top view of an artificial vertebral body of the present invention.
Figure 47:
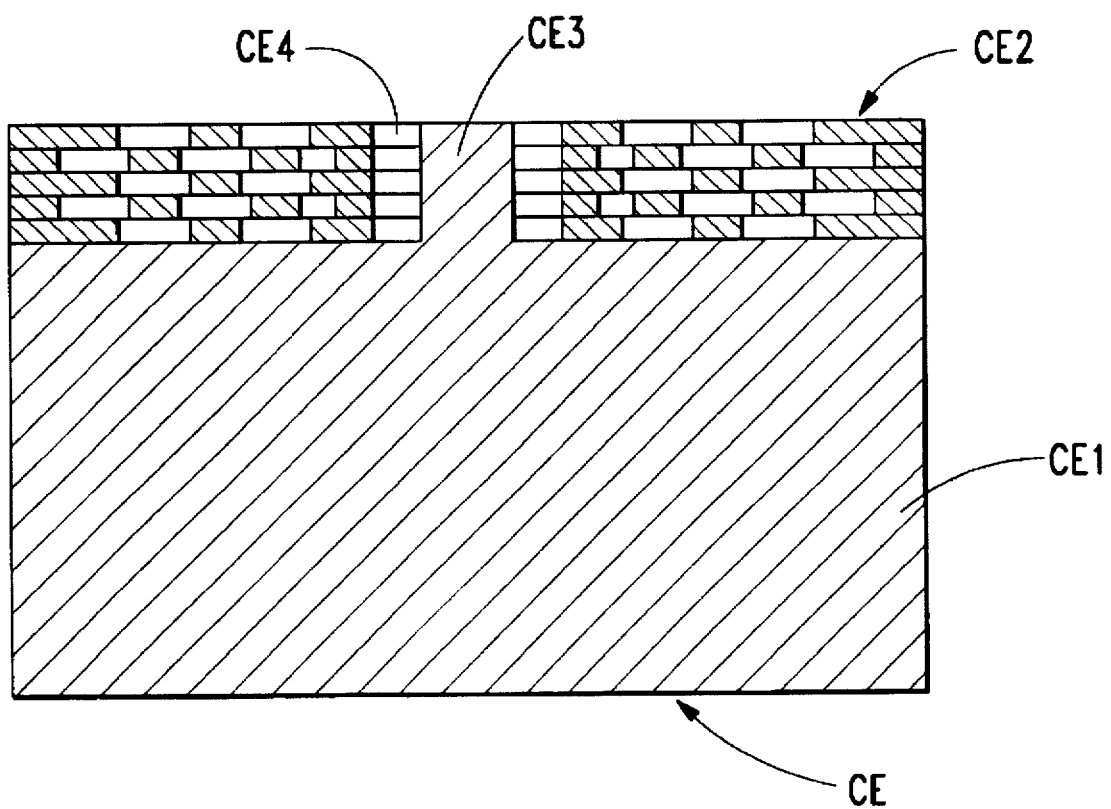
FIG. 47 is a sectional view taken on line V—V of FIG. 46.

FIG. 46 is a top view of the artificial vertebral body CE used as a prosthesis of the present invention. The porous lamination component CE2 has most densely arranged through holes H with an effective diameter of 300 μm to form three-dimensional pores as shown in FIG. 47. At the almost central section of the end surface of the main body CE1, a joint-use cylinder CE3 measuring 0.98 mm in height and 2 mm in diameter is projecting. Around the internal circumference of the above-mentioned porous lamination component CE2, six deformation absorbing grooves CE4 are disposed so as to enclose the joint-use cylinder CE3. The pressure-fit surface CE5 making contact with the joint-use cylinder CE3 has a circular shape with a diameter of 2.3 mm. When each titanium thin sheet is placed on the end surface of the main body CE1, the pressure-fit surface CE5 functions to firmly make contact with the joint-use cylinder CE3.

FIG. 47 is a sectional view taken on line V—V of FIG. 46. The above-mentioned porous lamination component CE2 is supported and secured by the joint-use cylinder CE3 of the main body CE1. This assembly is then heated to about 900° C. in the vacuum furnace so that the titanium thin sheets causes diffusion bonding. When paste including titanium particles is applied to the end surface of the above-mentioned main body CE1, the titanium particles combine with the metallic atoms of the porous lamination component CE2. In addition, the melted titanium of the thin sheets penetrates the small through holes disposed in the alumina ceramics of the main body CE1 at the end surface thereof to provide an anchoring effect. As a result, the joint between the porous lamination component CE2 and the main body CE1 is further enhanced.

The prosthesis of this example can be widely applied to the structures for surfaces making contact with bone tissues, such as femoral bone components of artificial knee joints made of ceramics, tibia components, iliac bone spacers, cranial bone prostheses and rib pins.

TABLE 5

| Two groups | After 2 weeks | | After 6 weeks | |
|---|---|---|---|---|
| compared | Value p | Judgment | Value p | Judgment |
| S1 <-> S2 | 0.024 | * | — | ns |
| S1 <-> S3 | 0.0003 | **** | 0.792 | ns |
| S1 <-> S4 | 0.017 | * | — | ns |
| S2 <-> S3 | 0.378 | ns | 0.811 | ns |
| S2 <-> S4 | 0.672 | ns | — | ns |
| S3 <-> S4 | 0.841 | ns | 0.792 | ns |

After the adhesion strength tests, the bone block was fixed by a 10% neutral buffer formalin water solution and dehydrated by ascending-row ethanol, then embedded with polyester resin. The bone block was sliced at the central section of the porous lamination component thereof and at the portions 4 mm away from the central section in the direction perpendicular to the longitudinal axis of the bone block. The slices obtained in this way were ground to a thickness of about 70 to 80 μm. The nondecalcified ground slices were subjected to toluidine blue dyeing and the degree of penetration of osteoblast was examined by light microscopy. FIG. 18 shows a light microscopic image. The depth from the surface CS proximal to the existing cortical bone CB shown in the figure to the surface of the porous lamination component, that is, the penetration depth BD of the osteoblast's leading end from the surface P1 of the porous lamination component to the thin sheet 10, for example, was compared with the depth PD of the porous layer to obtain the ratio BI of BD to PD.

Example 7

Figure 48:
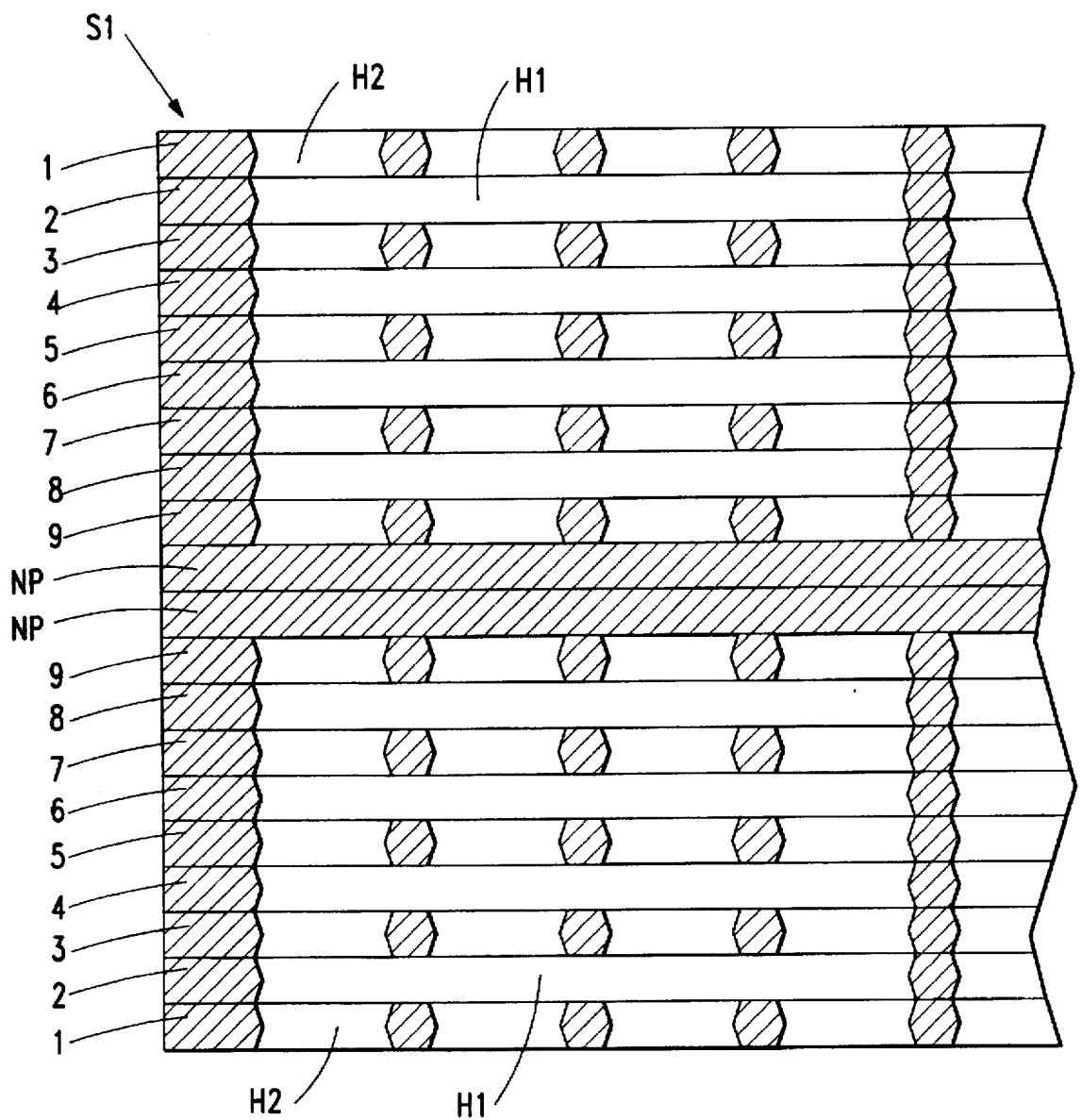
FIG. 48 is a vertical sectional view of the porous lamination component of a further example of the present invention.

This example is a further developed embodiment of example 2. A porous lamination component S1 of this example has an appearance as shown in FIG. 1 and a sectional view as shown in FIG. 48. The lamination component S1 is made of pure titanium and comprises two high-density thin sheets NP laminated each other at the central layer portion thereof for the purpose of reinforcement, and nine thin sheets including two types of thin sheets: five thin sheets n (n=an odd number) having a plurality of smaller through holes $H_1$ and four thin sheets n+1 having a plurality of larger through holes $H_2$, these two types of thin sheets being laminated alternately, and the nine thin sheets being further laminated to both outer sides of the laminated high-density thin sheets NP. All the above-mentioned thin sheets NP, n and n+1 have a thickness of 100 μm. The method of making this porous lamination component S1 conforms to that used to make example 1.

Figure 49:
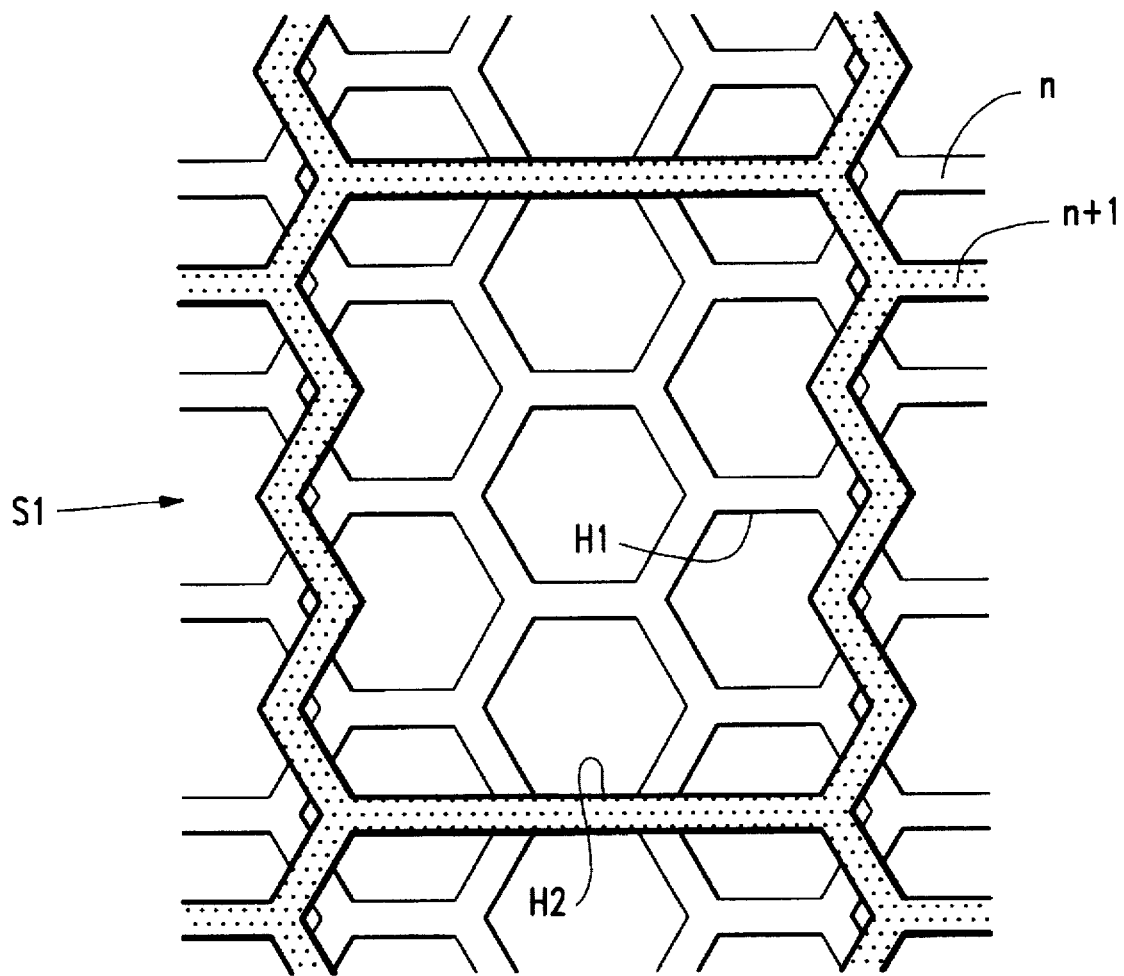
FIG. 49 is a plan view illustrating one example of two adjacent, vertically laminated thin sheets in accordance with the example illustrated in FIG. 48.

FIG. 49 shows a plan view illustrating two adjacent, vertically laminated thin sheets n and n+1. As shown in the figure, a larger through hole $H_2$ encloses three smaller through holes $H_1$ and communicates with 11 smaller through holes $H_1$ including the three enclosed through holes $H_1$ in the plan view. The smaller through hole $H_1$ has the shape of a regular hexagon in the plan view and the inscribed circle thereof has a diameter of 350 μm. On the other hand, the inscribed circle of the larger hole $H_2$ has a diameter of 1,000 μm. The volume porosity of the above-mentioned porous lamination component S1 is 70%.

Figure 50:
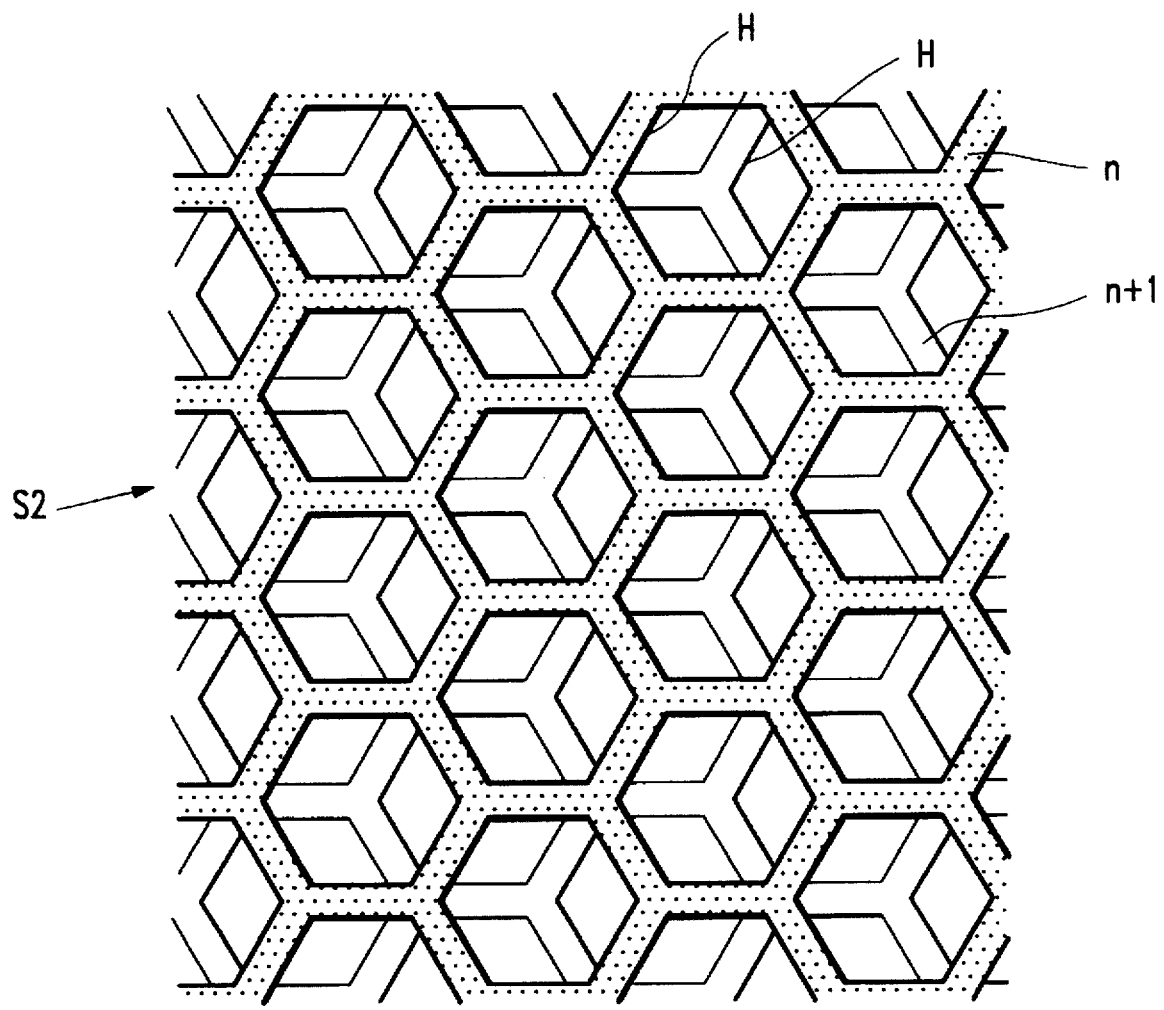
FIG. 50 is a plan view illustrating another example of two adjacent, vertically laminated thin sheets in accordance with the example illustrated in FIG. 48.
Figure 51:
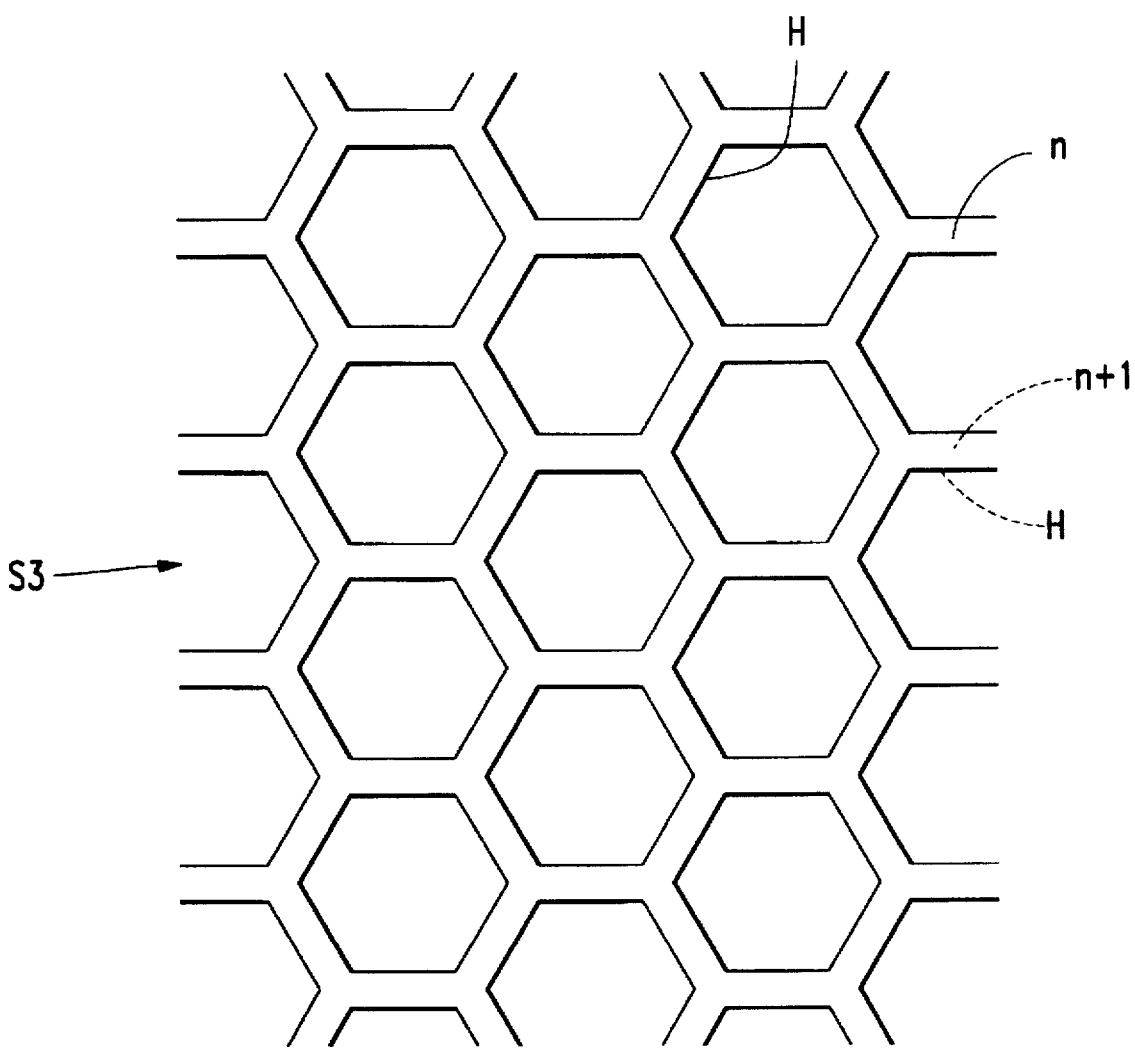
FIG. 51 is a plan view illustrating still another example of two adjacent, vertically laminated thin sheets in accordance with the example illustrated in FIG. 48.

In addition, another type of this example, a porous lamination component S2, was made. Although it is almost the same as the above-mentioned porous lamination component S1, as shown in FIG. 50, two adjacent, vertically laminated thin sheets n and n+1 have through holes H having the same shape, that is, a regular hexagon with an inscribed circle diameter of 350 μm. The two thin sheets are, however, laminated such that a through hole H disposed in the thin sheet n uniformly communicates with three through holes H disposed in the other thin sheet n+1 (volume porosity=about 80%). Furthermore, still another type of this example, a porous lamination component S3, was made. As shown in FIG. 51, two adjacent, vertically laminated thin sheets n and n+1 have through holes H having the same shape, that is, a regular hexagon with an inscribed circle diameter of 350 μm. The two thin sheets are laminated such that all through holes H disposed in the thin sheet n almost completely overlap with all through holes H disposed in the other thin sheet n+1 (volume porosity=about 80%).

Comparison Example

Figure 52:
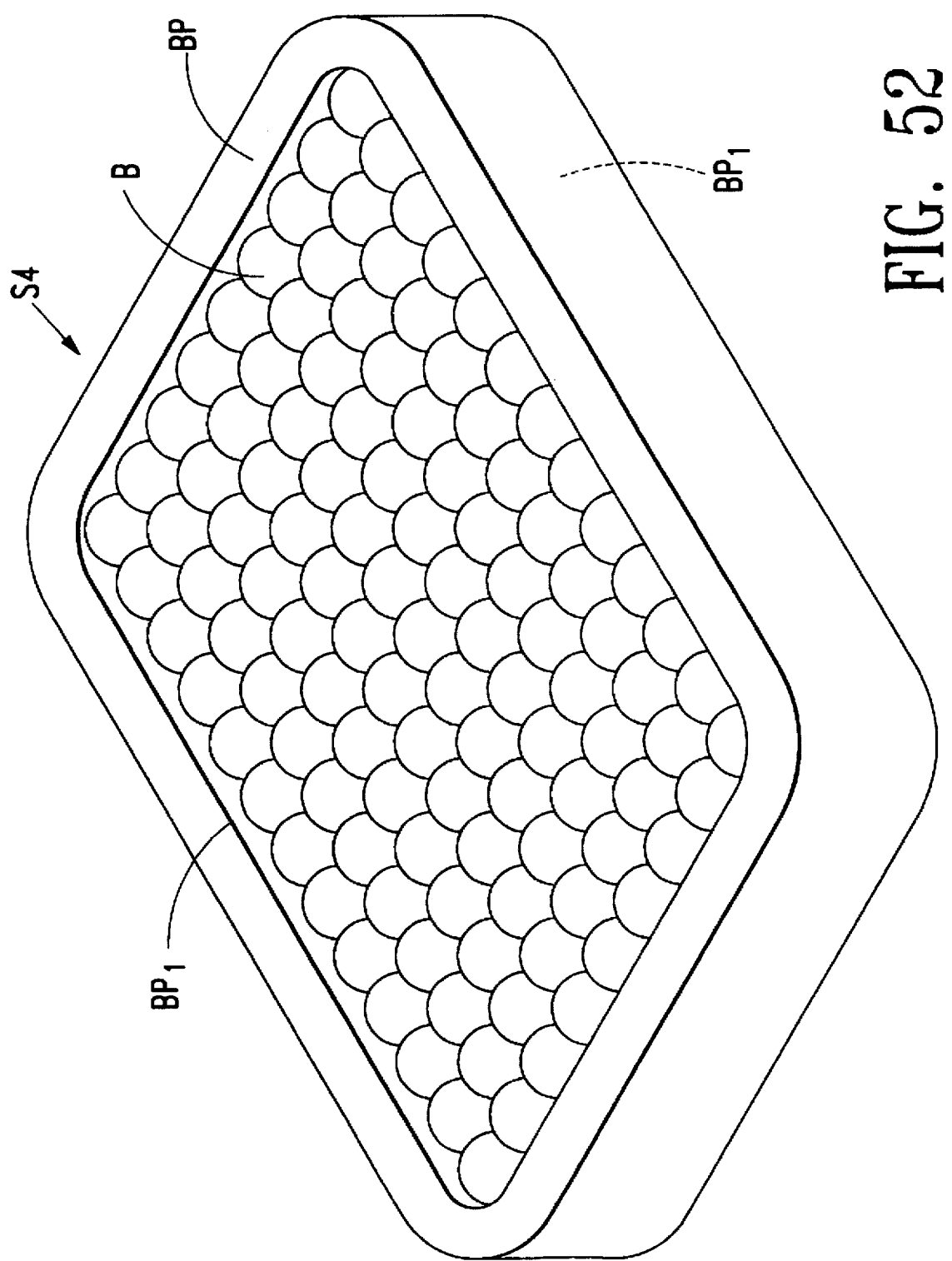
FIG. 52 is a perspective view of the porous lamination component of a still further example of the present invention.

As an example used for comparison with the porous lamination components of the above-mentioned example 7, a porous lamination component S4 (volume porosity=about 40%) was made as shown in FIG. 52. The external size of the porous lamination component S4 is almost equal to that of the porous lamination components S1 to S3 of the above-mentioned example 6. It was made by disposing pure titanium beads B with a diameter of about 500 μm all over the convex sections $BP_1$ formed on the top and bottom of the base body BP made of an alloy comprising titanium/8-aluminum/4-vanadium and by bonding the beads B at high temperature. The narrowest bore formed among the beads of this porous lamination component S4 was about 100 μm.

Animal Experiment 2

The same experiment as the above-mentioned animal experiment 1 was conducted by using the porous lamination components S1 to S3 of the above-mentioned example 6 and the comparison example, that is, the porous lamination component S4.

Figure 53:
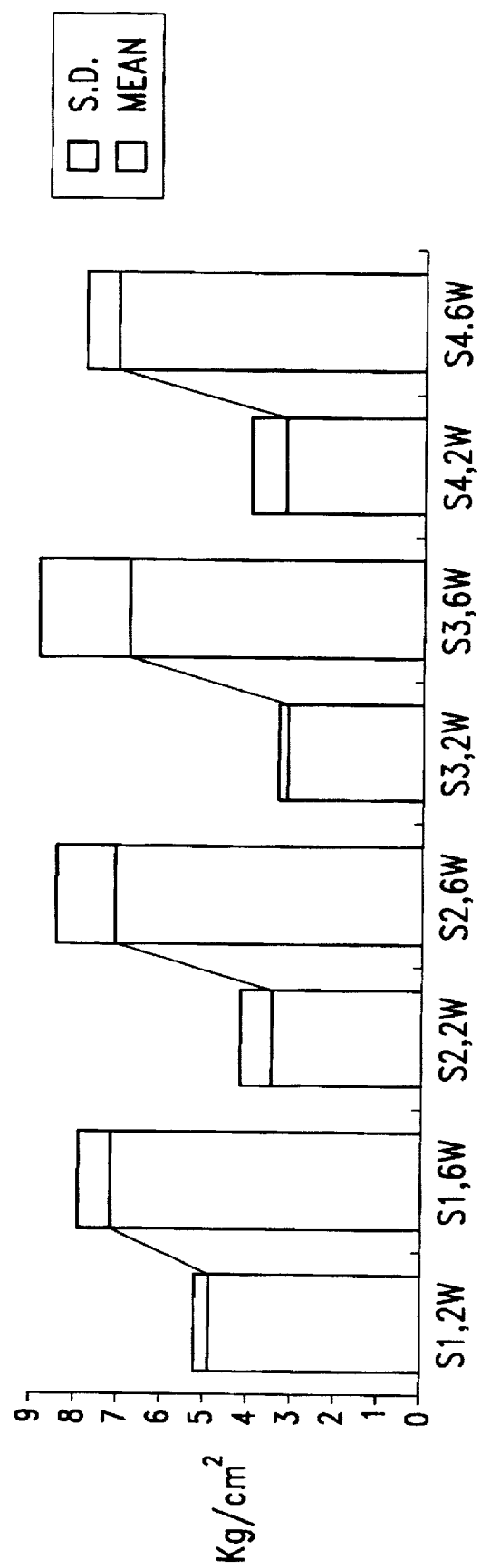
FIG. 53 is a graph illustrating the results of adhesion strength tests performed on the porous lamination components illustrated in FIGS. 49–52.

According to the measurement results of adhesion strength T shown in FIG. 53, the adhesion strength values of the porous lamination components S1 to S4 reached about 7 kg/cm² after two weeks and no significant difference was recognized among them. After six weeks, however, the porous lamination component S1 showed a significant difference from the porous lamination components S2 to S4.

Table 5 shows significant difference verification values p of the strength of adhesion between two groups of the porous lamination components measured after two and six weeks. (How to obtain p values) In the judgment column of Table 5, judgment marks are represented according to value p. When $0.01 \leq p < 0.05$, mark * is placed. When $0.005 \leq p < 0.01$, mark  is placed. When $0.001 \leq p < 0.005$, mark * is placed. When $p < 0.001$, mark **** is placed. When there is no statistical significance, that is, when $p \geq 0.05$, mark ns is placed.

[Table 5]

Next, formalin-fixed noncalcified sliced samples of bone/porous lamination components were subjected to toluidine blue dyeing. By obtaining the areas of dyed calcified tissues, the depth ratio of bone tissue penetration into pores and the volume ratio BP of the penetrated bone tissues were obtained. There results are shown in FIGS. 54 and 55.

Figure 54:
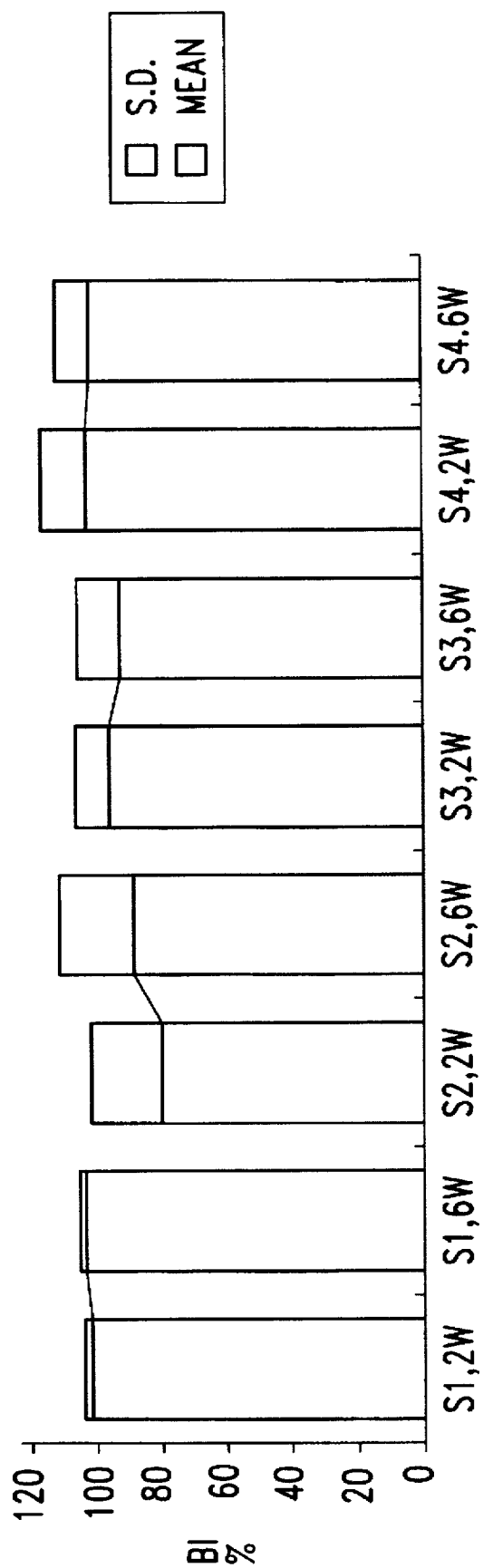
FIGS. 54 and 55 illustrating the results of dye tests conducted on the lamination components illustrated in FIGS. 49–52.

As obviously shown in FIG. 54, the penetration depth ratios for the porous lamination components S1 to S4 were 80% or more. After two weeks, the values for the two porous lamination components S1 and S3 of example 6 become particularly large.

Figure 55:
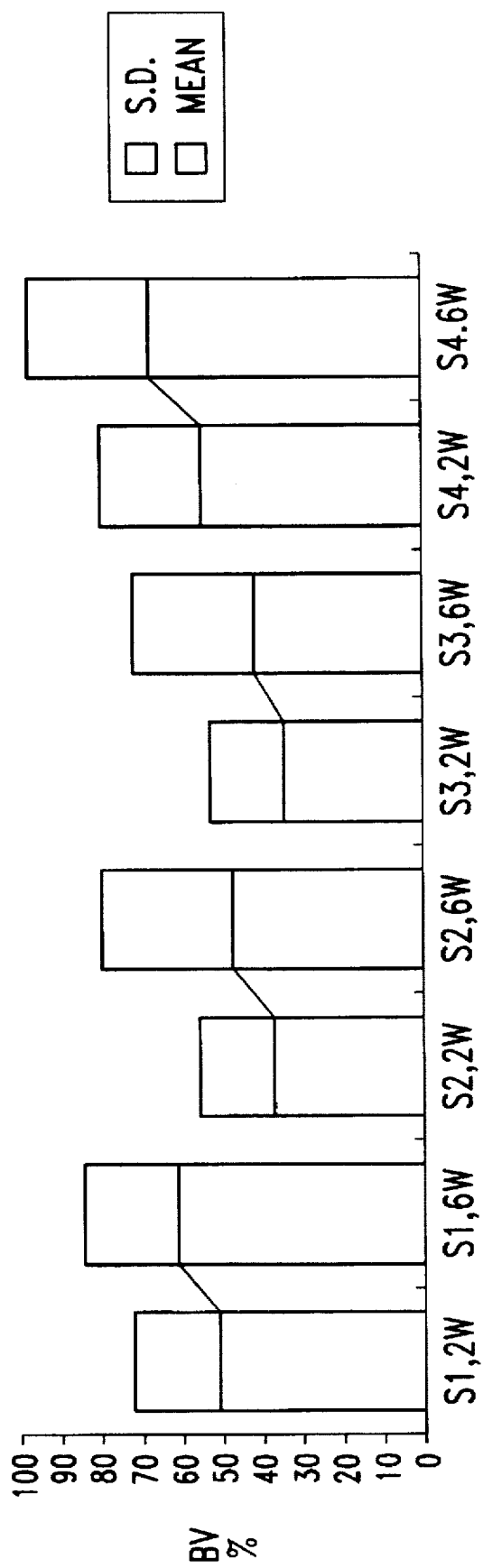

Furthermore, as obviously shown in FIG. 55, the volume ratios for the porous lamination components S1 to S4 were more than 40%. It is thus found that large amounts of bone tissues have been penetrated.

Next, the ground samples of the above-mentioned bone/porous lamination components were made and these were examined at 50 magnifications. According to the results, the porous lamination components S1, S2 and S3 of example 6 and the porous lamination component of S4 of the comparison example included both bone and marrow tissues inside thereof. In particular, the porous lamination component S1 also included vessel tissues. It is thus found that proper bone tissues will be expected to be maintained for an extended period of time. The porous lamination component S2 showed a low penetration depth ratio and the porous lamination components S3 and S4 were lacking in continuity in the lateral direction, indicating that sufficient nourishment supply is difficult.

Judging from the above-mentioned results, it is estimated that nourishment supply due to the penetration of vessel, bone and marrow tissues is very important to properly maintain the bone tissues inside the porous lamination components.

The prosthesis of the present invention can be firmly joined to living tissues by allowing the surrounding living tissues to promptly enclose the surfaces of the prosthesis after replacement and to penetrate the pores in the porous lamination component of the prosthesis and grow in the pores, thereby enhancing the durability of the prosthesis. Consequently, the present invention can provide prostheses which are not required to be replaced again, thereby imposing a less burden to patients.

Example 8

Figure 56A:
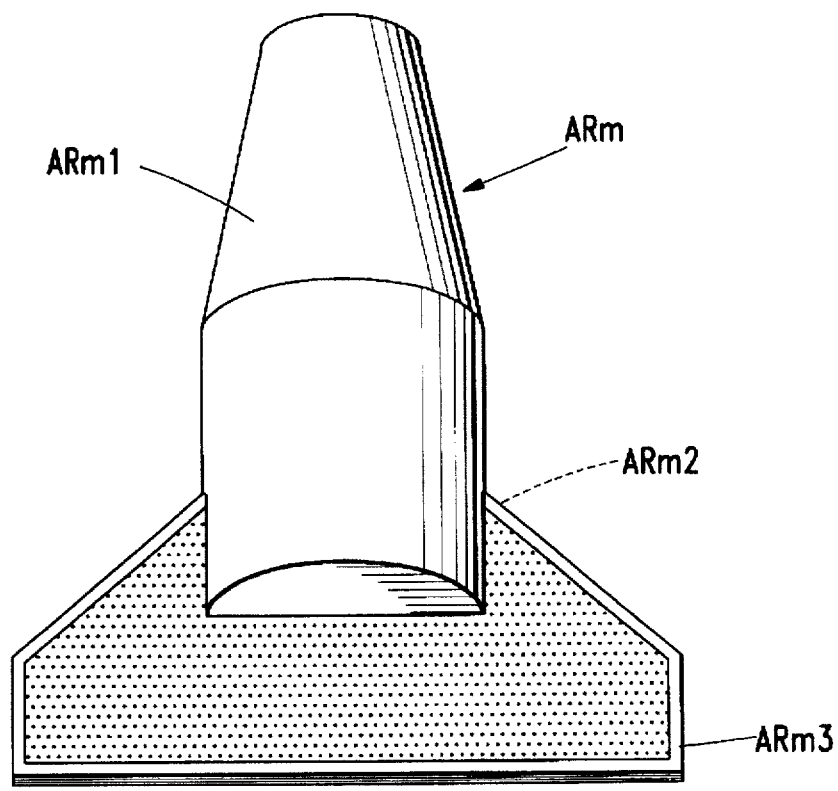
FIG. 56(a) is a perspective view illustrating an example of the artificial dental root of the present invention and FIG. 56(b) is a plan view illustrating a thin sheet constituting the porous lamination component formed at the artificial dental root.

The perspective view of this example, FIG. 56(a), shows a blade-shaped artificial dental root ARm for this example. This artificial dental root ARm comprises a metallic substantially-cylindrical post section ARm1 and a metallic porous lamination component ARm3 being fit in the fitting groove ARm2 formed in the diametric direction of the lower end section of the post section ARm1.

Figure 56B:
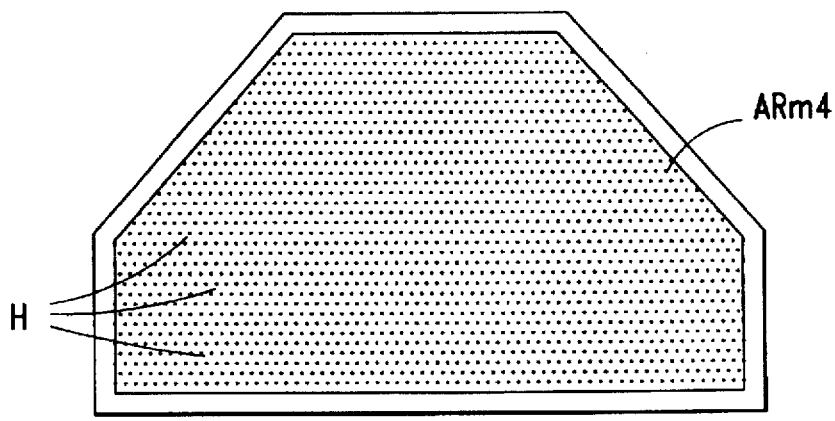

The porous lamination component ARm3 is made by laminating thin sheets ARm4 having a plurality of through holes H and then by sintering and securing the laminated thin sheets in a vacuum furnace as shown in the plan view of this example, FIG. 56(b).

We claim:

1. A method of making a prosthesis for the replacement of hard tissues of human bones and joints comprising the following steps of:
    perforating metal thin sheets, each having a thickness of 150 μm or less to provide a plurality of through holes, and being unharmful to the living body;
    laying said metal thin sheets thus obtained over one another so that said through holes may communicate with one another in the direction of the thickness thereof; and
    diffusion-bonding between said metal thin sheets into one body by heating so as to form a porous lamination component for the prosthesis.

2. A method of making a prosthesis for the replacement of hard tissues of human bones and joints according to claim 1, wherein at least one of said steps of laying and diffusion-bonding are performed at a desired surface portion of the base of the prosthesis of an artificial bone or joint.

3. A method of making a prosthesis for the replacement of hard tissues of human bones and joints comprising the following steps of:
    perforating metal thin sheets, each having a thickness of 150 μm or less to provide a plurality of through holes, and being unharmful to the living body, wherein the metal being unharmful to the living body is a titanium alloy, Co—Cr—Mo alloy or Fe—Ni—Cr alloy;
    laying said metal thin sheets thus obtained over one another so that said through holes may communicate with one another in the direction of the thickness thereof; and
    diffusion-bonding between said metal thin sheets into one body by heating substantially at no load so as to form a porous lamination component for the prosthesis.

4. A method of making a prosthesis for the replacement of hard tissues of human bones and joints comprising the following steps of:
    perforating metal thin sheets, each having a thickness of 150 μm or less to provide a plurality of through holes, and being unharmful to the living body:
    laying said metal thin sheets thus obtained over one another so that said through holes may communicate with one another in the direction of the thickness thereof; and
    diffusion-bonding between said metal thin sheets into one body by heating substantially at no load so as to form a porous lamination component for the prosthesis, wherein a single hole formed in at least one of a pair of said thin sheets being vertically adjacent to each other communicates with a plurality of holes formed in the other of the pair in the plan view direction of said thin sheets.

5. A method of making a prosthesis for the replacement of hard tissues of human bones and joints according to claim 3 or claim 4, wherein at least one of said steps of laying and diffusion-bonding are carried out at a desired surface portion of the base of an artificial bone or joint.

* * * * *